(12) United States Patent
Wu et al.

(10) Patent No.: US 8,404,930 B2
(45) Date of Patent: Mar. 26, 2013

(54) METHODS FOR IMPROVING MONOCOT TRANSFORMATION

(75) Inventors: Xinli E. Wu, Johnston, IA (US);
Myeong-Je Cho, Alameda, CA (US);
Zuo-Yu Zhao, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 332 days.

(21) Appl. No.: 12/694,013

(22) Filed: Jan. 26, 2010

(65) Prior Publication Data

US 2010/0192253 A1 Jul. 29, 2010

Related U.S. Application Data

(60) Provisional application No. 61/147,367, filed on Jan. 26, 2009.

(51) Int. Cl.
*C12N 15/84* (2006.01)
*A01H 4/00* (2006.01)

(52) U.S. Cl. ............ 800/294; 800/300; 800/320.1; 800/320.2; 800/320.3; 435/424; 435/430.1; 435/431; 435/469

(58) Field of Classification Search .................. None
See application file for complete search history.

(56) References Cited

U.S. PATENT DOCUMENTS

| | | | |
|---|---|---|---|
| 5,981,840 A | 11/1999 | Zhao et al. | |
| 6,369,298 B1 | 4/2002 | Cai et al. | |
| 6,486,384 B1 | 11/2002 | Zhang et al. | |
| 6,541,257 B2 | 4/2003 | Lemaux et al. | |
| 7,102,056 B1 | 9/2006 | Lemaux et al. | |
| 7,238,862 B2 * | 7/2007 | Allison et al. | 800/294 |
| 2006/0174367 A1 | 8/2006 | Zhang et al. | |
| 2007/0163007 A1 | 7/2007 | Ishida | |
| 2009/0263902 A1 | 10/2009 | Mehlo et al. | |
| 2009/0293157 A1 | 11/2009 | Mehlo et al. | |

FOREIGN PATENT DOCUMENTS

| | | | |
|---|---|---|---|
| WO | WO 97/48814 | * | 12/1997 |
| WO | WO 00/34491 A2 | | 6/2000 |
| WO | WO 03/062397 A2 | | 7/2003 |

OTHER PUBLICATIONS

Abumhadi, N., et al., "Callus Induction and Plant Regeneration From Barley Mature Embryos (*Hordem vulgare* L.)", Biotechnol. & Biotechnol. Eq. 19(3):32-37 (2005).
Carvalho, Carlos Henrique S., et al., "Agrobacterium-mediated Transformation of Sorghum: Factors That Affect Transformation Efficiency", Genetics and Molecular Biology 27(2):259-269 (2004).
Cho, M. et al., Poster P-2018 Sorghum Bombardment Transformation Poster, Congress on In Vitro Biology 38-A (2001).
Gao, Zhensheng et al., "Agrobacterium Tumefaciens-mediated Sorghum Transformation Using a Mannose Selection System", Plant Biotechnology Journal 3:591-599 (2005).
Gao, Zhensheng et al., "Efficient Genetic Transformation of Sorghum Using a Visual Screening Marker", Genome 48:321-333 (2005).
Howe, Arlene et al., "Rapid and Reproducible Agrobacterium-mediated Transformation of Sorghum", Plant Cell Rep 25:784-791 (2006).
Nguyen, Tuong-Van et al., "Agrobacterium-mediated Transformation of Sorghum (*Sorghum bicolor* (L.) Moench) Using an Improved in vitro Regeneration System", Plant Cell Tiss Organ Cult, 91(2) 155-164, published on-line Jul. 7, 2007.
Visarada, Kbrs et al., "Improvement of Sorghum Through Transgenic Technology" (Mar. 2007), printed from website http://www.isb.vt.edu/articles/mar0701.htm.

* cited by examiner

*Primary Examiner* — David T Fox
(74) *Attorney, Agent, or Firm* — Alston & Bird LLP

(57) ABSTRACT

The invention provides improved plant transformation methods. In particular the method provides increased transformation frequency, especially in recalcitrant plants. The method includes various transformation protocols for monocots, such as maize and sorghum, using a combination of media and light conditions to achieve increased efficiency of monocot transformation and increased callus initiation frequencies.

26 Claims, No Drawings

METHODS FOR IMPROVING MONOCOT TRANSFORMATION

CROSS-REFERENCE TO RELATED APPLICATIONS

This application claims priority under 35 U.S.C. §119 of a provisional application Ser. No. 61/147,367 filed Jan. 26, 2009, which application is hereby incorporated by reference in its entirety.

FIELD OF THE INVENTION

This invention relates to systems and methods for increasing transformation frequency/efficiency, and increasing the efficiency of plant regeneration.

BACKGROUND OF THE INVENTION

High efficiency transformation of plants is important in analyzing the usefulness of a variety of genes. Further high efficiency transformation of monocots is also important because large numbers of transgenic plants are needed to study the effect of a particular gene within a given period of time. The ability to directly transform agronomically important plant species at a usable frequency and across a wide range of genetic diversity is important for the development of commercial hybrid products with improved traits including, but not limited to, insect resistance, disease resistance, herbicide resistance, increased yield, increased tolerance to environmental stresses (such as drought, heat, etc.), enhanced seed quality (such as increased or modified starch, oil and/or protein content), and the like.

Genetic improvement of various crop species by genetic engineering has sometimes been hindered because techniques for in vitro culture, transformation, and regeneration of model cultivars are less effective with commercial cultivars. It would be of great benefit to improve the ability to genetically engineer monocots such as maize and sorghum to increase nutritional value, increase resistance to pests, diseases and environmental stress, and to enhance alternative uses.

Additionally, demands for food and fodder are increasing in developing countries in light of growing stress due to population and environment. For example, over the period between 1950 and 1980, the increase in maize production worldwide outpaced both wheat and rice. Despite a temporary downswing in the early to mid-1980's, due to both environmental and political factors, world maize production has risen steadily from around 145 million tons in 1950 to nearly 500 million tons by 1990. Increases in yield and harvested area have been the predominant contributors to enhanced world production; with yield playing the major role in industrialized countries and area expansion being most important in developing countries. Yet, over the next ten years it is also predicted that meeting the demand for corn worldwide will require an additional 20% over current production (Dowswell, C. R., Paliwal, R. L., Cantrell, R. P. (1996) Maize in the Third World, Westview Press, Boulder, Colo.).

Sorghum (*Sorghum bicolor* (L.) Moench) is a widely grown grain and forage crop, and is more closely related than rice to the major crops of tropical origin such as maize, sugarcane, and pearl millet. Sorghum ranks fifth worldwide in production among cereal crops, and is an important model for tropical grasses of worldwide importance. It is unique among major cereals because it adapts well to environmental extremes, notably drought and heat. These attributes make sorghum the logical grain to support human and animal populations in areas with extreme heat and minimal precipitation. Even in the absence of drought, water availability is an emerging problem that will affect at least six billion people worldwide by 2025. Increased demand for limited fresh water, coupled with global climate trends, and expanding populations, will increase the attractiveness of dry land crops such as sorghum. Moreover, it is second only to maize within the U.S. as a feedstock for ethanol production.

Several laboratories have reported successful but low rates of transformation frequency in sorghum utilizing particle bombardment (Able et al. 2001, In Vitro Cell Dev Biol, 37:341; Casas et al. 1993, Proc Natl Acad Sci., USA 90: 11212) or *Agrobacterium*-mediated transformation with the bar gene (Zhao et al. 2000, Plant Mol Biol 44:789) or the nptII gene (Tadesse et al. 2003, Plant Cell Tissue Organ Cult 75:1, Howe et al., 2006 Plant Cell Rep.; 25:784-791) as selectable markers. Recently, an *Agrobacterium*-based system was coupled with a visual marker gene selection strategy to identify sorghum transformants (Gao Z, Jayaraj J, Muthukrishnan S, Claflin L, Liang G H (2005) Genome 48:321). The microprojectile systems previously reported are hampered by reproducibility and relatively low efficiencies. On the other hand, *Agrobacterium*-mediated transformation is relatively efficient for sorghum using the 'super binary' vector system (Ishida et al. 1996, Nat Biotechnol: 14:745), short subculture intervals, and the addition of PVPP to tissue culture media (Zhao et al. 2000, Plant Mol. Biol 44:789). These latter two steps help block the negative impacts of associated phenolic production from sorghum tissue. Demonstration of standard binary plasmids being suitable for *Agrobacterium*-mediated transformation of sorghum (Gao et al. 2005 Genome 48:321) and a novel *Agrobacterium* vector (Howe et al. 2006, Plant Cell Rep.; 25:784-791) are reported.

Even with the advances listed above, transformation frequencies in sorghum are low and reported to average 1% and be as high as 5% (Nguyen et al., 2003, Plant Cell Tiss Organ Cult. DOI 10.1007/s11240-007-9228-1). Visarada and Kishore report that transformation followed by regeneration remains extremely complicated in sorghum transgenic technology. (Infor. Syst. for Biotech. March, 2007; pp. 1-3). There is a need, therefore, for efficient methods for transformation and regeneration that can be used with sorghum as well as a wide variety of monocots.

BRIEF SUMMARY OF THE INVENTION

Improved methods and systems for plant transformation and regeneration are provided herein. The examples below detail the application of these methods and systems to monocots, including commercially important crops and genotypes that have proven difficult or impossible to transform and regenerate by previously available methods. These improved methods result in significantly increased transformation frequency and increased efficiency of plant transformation, which are advantageous, especially when stacking genes. The methods can be used for transformation and regeneration of monocot plant species including, but not limited to, oat, wheat, maize, rice, sorghum, rye, sugarcane, barley, triticale, orchardgrass, tall fescue, red fescue, creeping bentgrass, Kentucky bluegrass, perennial ryegrass, switchgrass, *Miscanthus* and the like.

In one embodiment a method for transforming a monocot plant cell is provided. This method includes introducing a nucleic acid into the monocot plant cell of an explant by *Agrobacterium*-infection to produce an infected plant cell and co-cultivating the infected plant cell on a co-cultivation medium. The co-cultivation medium includes an auxin and copper and optionally a cytokinin. The transformed cell is rested on a resting medium to produce transformed tissue expressing the nucleic acid. The method also includes selecting for transformed tissue expressing the introduced nucleic acid on a selection medium and regenerating the transformed tissue on a regeneration media to produce a transformed monocot plant.

In yet another embodiment, a method of increasing callus initiation frequency is provided. This method includes co-cultivating an *Agrobacterium*-infected plant cell on a co-cultivation medium. The co-cultivation medium includes an auxin and copper. The method further includes resting the infected cells on a resting medium. This method also increases the quality of callus obtained.

In still another embodiment, a combined media system for use with any of the methods described herein is provided. The media system includes the use of a co-cultivation medium, a resting medium and optionally a selection medium. The co-cultivation medium includes an auxin and copper and the medium may be used for co-cultivating an *Agrobacterium*-infected plant cell. The resting media may be employed to rest the infected cells to produce transformed tissue, such as callus. The selection medium may be used to select the transformed tissue expressing the nucleic acid. Preferably, the various steps of co-cultivating, resting and selecting are carried out using the combined media system. In another embodiment, a plant transformed by any of these methods or systems is provided.

The foregoing and other aspects of the invention will become more apparent from the following detailed description.

DETAILED DESCRIPTION OF THE PREFERRED EMBODIMENTS

All references referred to are incorporated therein by reference.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not intended to limit the scope of the invention.

A combined media system and methods for the tissue culture and for the transformation of monocots are provided herein. Methods for increasing transformation efficiency/frequency, increasing callus quality, increasing callus initiation frequency, increasing callus induction frequency, increasing the growth rate of plant regeneration, and deceasing plant regeneration time are also described. Generally, the methods include culturing a plant cell of an explant in an altered environment, for example, by altering the kinds and amount of various plant hormones or metal in the culture medium and/or levels and duration of exposure to light.

Contrary to known teachings that transformed plant cells cultured in dim light on medium containing an auxin, a cytokinin, and copper have improved callus quality and regenerability, the methods herein describe novel methods for increasing transformation efficiency/frequency for monocots by culturing the plant cell in dark conditions on a medium that includes an auxin and copper and preferably omits cytokinins.

In one embodiment, the methods include introducing a nucleic acid into the plant cell of the explant to produce a transformed plant cell. Any suitable explant may be used in the methods described herein. As used herein, the term "explant" includes a plant tissue such as callus, immature and mature embryo, immature and mature seed, meristem, cell clusters, scutella, nodes, young leaf bases, hypocotyl explants, roots, inflorescences, suspension cultures, cultures of suspended cell aggregates, meristematic regions, leaves, green tissue, non-green tissue, somatic embryos and shoot apexes and the like. As known to one skilled in the art, the explant may be obtained from any number of sources. For example, embryos can be obtained from the fertilized reproductive organs of a mature maize plant. See Green and Phillips (Crop Sci. 15:417-421, 1976). Maize immature embryos can be isolated from pollinated plants, as another example, using the methods of Neuffer et al. ("Growing Maize for genetic purposes." In: Maize for Biological Research W. F. Sheridan, Ed., University Press, University of North Dakota, Grand Forks, N. Dak. 1982). Any nucleic acid of interest can be used in the methods of the invention. For example, a monocot plant can be engineered to express disease and insect resistance genes, genes conferring nutritional value, genes increasing yield or stability, genes to confer male and/or female sterility, antifungal, antibacterial or antiviral genes, and the like. As appreciated by one ordinarily skilled in the art, it is possible to introduce a nucleic acid into a plant cell using any suitable method, for example, *Agrobacterium*-infection, electroporation, particle bombardment-mediated transformation, whisker-mediated transformation, microinjection and the like.

The method further includes culturing the transformed plant cell in light conditions, dim conditions, dark conditions or a combination thereof. The term "light conditions" include, but are not limited to, light conditions having a light intensity greater than about 30 $\mu E\ m^{-2}\ sec^{-1}$, e.g. 40 $\mu E\ m^{-2}\ sec^{-1}$, 50 $\mu E\ m^{-2}\ sec^{-1}$, 60 $\mu E\ m^{-2}\ sec^{-1}$, 70 $\mu E\ m^{-2}\ sec^{-1}$ or more. The term "dim conditions" include, but are not limited to, light conditions having a light intensity from about 10 $\mu E\ m^{-2}\ sec^{-1}$ to about 30 $\mu E\ m^{-2}\ sec^{-1}$. The term "dark conditions" include, but are not limited to, those conditions such as found in a dark room (e.g. a special tissue culture room maintained at certain temperature and moisture) or in a tissue culture incubator without lighting provided, or with lighting that can be controlled, such as a Percival incubator. Dark conditions may comprise, but are not limited to, for example, times of partial light, intermittent light and times of complete light, where the times of dark may comprise less than 1 hour/24 hours, preferably where the times of dark may comprise less than 45 minutes/24 hours, more preferably where the times of dark may comprise less than 30 minutes/24 hours, even more preferably where the times of dark may comprise less than 15 minutes/24 hours. Dark conditions may comprise times of light wherein the transformation conditions were being checked, media changed, explants moved or normal laboratory experimental protocols were being conducted. This may include any steps in standard tissue culturing as understood by one of skill in the art, including co-cultivating, resting, selecting and/or regenerating. Dark conditions include light conditions of less than 10 $\mu E\ m^{-2}\ sec^{-1}$, preferably less than 8 $\mu E\ m^{-2}\ sec^{-1}$, and more preferably less than 5 $\mu E\ m^{-2}\ sec^{-1}$. Dark conditions may include no more than 10% of the time of any one or more of the culturing steps in the light, preferably no more than 8% of the time of any one or more of the culturing steps in the light, more preferably no more than 5% of the time of any one or more of the culturing steps in the light, even more preferably no more than 3% of the time of any one or more of the culturing steps in the light, even more preferably no more than 1% of the time of any one or more of the culturing steps in the light. Dark conditions include at least 68 contiguous hours, preferably dark conditions comprise at least 70 contiguous hours, more preferably dark conditions comprise at least 72 contiguous hours.

The transformed plant cell may be cultured on culture media in dark conditions to produce a transformed tissue, e.g. non-green tissue. As used herein, the term "culturing" refers to putting plant cells on a culture medium, for example, to maintain the cells, to initiate callus growth or to produce a tissue, plant and the like. Any suitable culture media that support the viability and growth of the plant cell or tissue, or the growth of whole plant specimens may used. The terms "media" and "medium" are used interchangeably herein and may refer to a solid or a liquid. Preferably, the culture medium supports the viability and growth of a transformed tissue. In one aspect, the culture medium includes copper, an auxin, a cytokinin or a combination thereof. The plant cells may be cultured using standard tissue culture methods known to one of skill in the art and as disclosed herein.

A. Preculturing the Plant Cells Prior to Transformation

In one aspect, culturing includes, but is not limited to, the steps of preculturing, co-cultivating, resting, selecting, regenerating, or rooting of the transformed monocot plant cells or combinations thereof. Prior to introducing into the monocot plant cells the nucleic acid, the monocot plant cells, such as immature embryo, may be precultured. "Precultured" or "preculturing", as used herein, means culturing the cells or tissues in an appropriate preculture medium to support plant tissue growth prior to the introduction of a nucleic acid, for example, via *Agrobacterium*-infection, electroporation, or particle bombardment. Preculturing the plant cells may be performed using any method and media known to one ordinarily skilled in the art. Such protocols may vary depending on the species of plant being transformed and the transformation technique employed, e.g. *Agrobacterium*-infection, electroporation, or particle bombardment. Preculturing medium that is suitable for preculturing plant cells may be purchased as a commercial preparation or custom prepared and modified by those of skill in the art. Examples of suitable medium for preculturing monocot plant cells include, but are not limited to, MS-based media (Murashige T and Skoog F (1962) A Revised Medium For Rapid Growth And Bioassays With Tobacco Tissue Cultures. Physiol Plant. 15(3): 473-497), LS salts-based media (Linsmaier, E and Skoog, F, (1965) Organic growth factor requirements of tobacco tissue culture. *Physiol. Plant.* 18:100-127), CM4C, M7, or N6-based media (Chu, Proc. Symp. Plant Tissue Culture. Peking: Science Press. Pp. 43-50, 1978), PHI-T, DBC1, DBC2, and DBC3 which may be supplemented as desired. When particle bombardment is employed as the transformation technique of choice, an osmotic medium, for example, medium for osmotic treatment of embryos, such as that described in Plant Cell Culture Protocols, edited by Victor M. Loyola-Vargas and Felipe Vazquez-Flota, Humana Press, 2006, Totowa, N.J., pp. 273-283, is preferred for the preculturing step. The preculturing step may be performed for as little as a few hours, such as 1 or 2, or for an extended period of time, for example, from about 1 to 7 days or more. In some cases, preculturing in combination with the resting and/or selecting steps described herein may increase the transformation frequency/efficiency. The terms "transformation frequency" and "transformation efficiency" are used interchangeably herein and refer to the number of the explants producing transgenic events divided by the total explants *Agrobacterium*-infected or bombarded or the number of explants that generate transgenic events divided by the number of explants infected by *Agrobacterium* or bombarded.

B. Co-Cultivating the *Agrobacterium*-Infected Plant Cells

When nucleic acids are introduced into the plant cells via *Agrobacterium*-infection, the plant cells may be co-cultivated on a co-cultivation medium. As used interchangeably herein, "co-cultivating", "co-cultivation", "co-culture" refers to incubating *Agrobacterium*-infected plant cells such as embryos or explants on co-cultivation medium to allow continued T-DNA delivery from *Agrobacterium* into plant cells.

The *Agrobacterium*-infected plant cell is co-cultivated in light, dim or dark conditions, typically for about 3 days. In some examples, the co-cultivation step may be carried out for more than 3 days, e.g. 4 days, and in some cases it may be less than 3 days. Preferably, the *Agrobacterium*-infected plant cell is co-cultivated in dark conditions for about 3 days or less. In one aspect, the dark conditions include exposing the plant cell to less than 10 $\mu E\ m^{-2}\ sec^{-1}$ of light. The plant cell is preferably exposed to less than 10 $\mu E\ m^{-2}\ sec^{-1}$ of light for 72 or less consecutive hours. The co-cultivation step may be carried out in dark conditions on any suitable co-cultivation media for any length of time so long as it is suitable for growing and culturing plant cells or callus tissue and allows for continued T-DNA transfer. Exemplary co-cultivation media include but are not limited to known media such as PHI-I, PHI-T, PHI-U, PHI-RF, PHI-Z and PHI-RR described in U.S. Pat. No. 5,981, 840 or U.S. Pat. No. 6,369,298, or described elsewhere herein. Other media suitable for co-cultivation include DBC1, DBC2, and DBC3 which are described in Examples 1 and 2 herein and in U.S. Pat. No. 7,102,056 incorporated by reference in its entirety. Use of PHI-T medium is preferred as it has been found to increase T-DNA delivery and efficiency in maize. See, for example, Example 8.

The co-cultivation medium or other media may include an additive such as, but not limited to, copper and an auxin. The co-cultivation medium may include copper or have additional copper from another source, for example, from MS salts. The concentration of copper in the co-cultivation medium may range from about 0.1 $\mu M$ to about 50 $\mu M$. In one embodiment, the co-cultivation medium comprises about 0.1 $\mu M$, 0.5 $\mu M$, 1 $\mu M$, 2 $\mu M$, 3 $\mu M$, 4 $\mu M$, 5 $\mu M$ or greater concentration of copper. Preferably, the co-cultivation medium has a low concentration of copper, for example, a copper concentration of about 0.1 $\mu M$ or less, such as the level present in typical plant growth media, such as MS medium. Any form of copper that provides nutritional source for plant tissue culture may be utilized including but not limited to salts or compositions containing copper e.g. cupric sulfate, copper chloride, copper nitrate, copper gluconate, or copper acetate.

Auxins may be included or added to the co-cultivation media. Exemplary auxins include, but are not limited to, 2,4-dichlorophenoxyacetic acid (2,4-D), dicamba, naphthaleneacetic acid (NAA), indoleacetic acid (IAA), picloram, 2,4,5-trichlorophenoxyacetic acid, 4-chloro-indoleacetic acid, phenylacetic acid (PAA) or indole-3-butyric acid (IBA) and the like and combinations thereof. The co-cultivation medium may include one or more auxins, such as 2,4-D, in an amount of about 0.01 mg/L to about 10 mg/L, preferably from about 0.01 mg/L to about 5 mg/L. In one embodiment, when co-cultivating monocot plant cells on a co-cultivation medium, the auxin such as 2,4-D is present in the co-cultivation media at concentrations of about 1.0 mg/L, 2.0 mg/L, 3.0 mg/L, 4.0 mg/L or 5.0 mg/L, 6.0 mg/L, 7.0 mg/L, 8.0 mg/L, 9.0 mg/L or 10.0 mg/L or greater. One example of an auxin for use in the methods is about 1.0 to about 2.0 mg/L of 2,4-D.

See Examples 1-2. Other auxins having a different concentration may be used in the co-cultivation medium depending on the genotype or explant.

The co-cultivation medium generally excludes cytokinins; however, optionally, the medium may include a concentration of cytokinin from about 0.01 mg/L, 0.2 mg/L, 0.3 mg/L, 0.4 mg/L, 0.5 mg/L 1 mg/L, 2 mg/L, 3 mg/L, 4 mg/L, 5 mg/L, 6.0 mg/L, 7.0 mg/L, 8.0 mg/L, 9.0 mg/L or 10.0 mg/L of the co-cultivation medium. Exemplary cytokinins include but are not limited to, 6-benzylaminopurine (BAP), zeatin, kinetin, 2iP or zeatin riboside and the like or combinations thereof. In some embodiments, concentrations of BAP are useful at about 0.01 mg/L as in DBC1 medium or about 0.5 mg/L as in DBC3 medium.

Preferably, the co-cultivation medium includes 0.0 mg/L to 0.01 mg/L of a cytokinin such as BAP in the co-cultivation medium. As shown in Examples 7-12, when transformed monocot plant cells are co-cultivated in dark conditions on medium of PHI-T increased or improved transformation frequency is observed. The composition of PHI-T is described elsewhere herein. Co-cultivating may be performed using any suitable techniques or protocols known to those of ordinary skill in the art.

C. Resting the Transformed Plant Cells

Transformed plant cells may be cultured in a resting step. "Resting", as used herein, refers to the culture step where plant cells, such as embryos, or other explants, are incubated after the introduction of the nucleic acid, for example, by electroporation, particle bombardment, or *Agrobacterium*-infection. For example, with respect to *Agrobacterium*-mediated transformation, the infected plant cells are typically incubated in a resting step after a period of co-cultivation. The resting step permits the preferential initiation and growth of callus from the transformed cells containing the heterologous nucleic acid and is usually carried out in the absence of any selective pressures. The transformed plant cells are subjected to a resting media that typically includes an antibiotic capable of inhibiting *Agrobacterium* growth. Such antibiotics are known in the art and include cefotaxime, timetin, vancomycin, carbenicillin, and the like. Concentrations of the antibiotic will vary according to what is standard for each antibiotic. For example, concentrations of carbenicillin will range from about 50 mg/L to about 250 mg/L, carbenicillin in solid media, preferably about 75 mg/L to about 200 mg/L, and more preferably about 100-125 mg/L. Those of ordinary skill in the art of monocot transformation will recognize that the concentration of antibiotic can be optimized for a particular transformation protocol without undue experimentation.

Any suitable resting media may be used with the methods of the invention so long as it allows for initiation and growth of callus from the plant cells, e.g. infected or transformed cells. Exemplary resting media include DBC3 and PHI-U without PPT, although the preferred resting medium is DBC3 medium. In addition, the resting medium may include an additive such as, but not limited to, copper, an auxin, or a cytokinin or a combination thereof. Exemplary forms of copper, auxins, or cytokinins are described elsewhere herein. In one aspect, copper is present in the resting medium at concentrations from about 0.1 µM to about 50 In one embodiment, the resting medium has about 1 µM, 2 µM, 3 µM, 4 µM, 5 µM, 10 µM, 15 µM, 20 µM, 25 µM, 30 µM, 35 µM, 40 µM, 45 µM, 50 µM or greater concentration of copper. Preferably the resting medium has equal to or greater than 5 µM of copper. Preferably, cupric sulfate is utilized.

The resting medium may include one or more auxins, such as 2,4-D, in an amount of about 0.01 mg/L to about 10 mg/L, preferably from about 0.01 mg/L to about 5 mg/L. In one embodiment, when resting monocot plant cells on a resting medium, the auxin such as 2,4-D is present in the resting medium at concentrations of about 0.1 mg/L, 0.2 mg/L, 0.3 mg/L, 0.4 mg/L, 0.5 mg/L, 11.0 mg/L, 2.0 mg/L, 3.0 mg/L, 4.0 mg/L or 5.0 mg/L, 6.0 mg/L, 7.0 mg/L, 8.0 mg/L, 9.0 mg/L or 10.0 mg/L or greater. One example of an auxin for use in the methods is 1.0 to 2.0 mg/L of 2,4-D. See Examples 1-2. Other auxins having a different concentration may be used in the resting medium.

In a preferred embodiment, a cytokinin, such as BAP, is present in the resting medium from about 0.01 mg/L to about 10 mg/L or greater, preferably from about 0.01mg/L to about 5 mg/L. For example, the concentration of BAP in the resting medium may be about 0.1 mg/L, 0.2 mg/L, 0.3 mg/L, 0.4 mg/L, 0.5 mg/L, 1 mg/L, 2 mg/L, 3 mg/L, 4 mg/L, 5 mg/L, 6 mg/L, 7 mg/L, 8 mg/L, 9 mg/L, 10 mg/L or greater. Most preferably, BAP is present in the resting medium at about 0.5 mg/L. In one embodiment, the resting medium includes DBC3 medium and may also include an additive of antibiotics, such as carbenicillin at 100 to 150 mg/L and the like.

Resting may be carried out in light, dim, or dark conditions as described elsewhere herein, e.g. dim conditions of light greater than 10 µE m$^{-2}$ sec$^{-1}$, preferably from about 10 to about 30 µE m$^{-2}$ sec$^{-1}$. The transformed cells are allowed to rest in light, dim, or dark conditions for about 1 to about 12 days, preferably for about 3-7 days, more preferably about 4 days. See, for example, Examples 1, 2 and 9-13. Resting of the transformed plant cells may be performed using any suitable techniques or protocols known to those of ordinary skill in the art.

D. Selecting the Transformed Plant Cells

In one embodiment, the method includes selecting for the transformed plant cells on a selection media. This step is typically performed subsequent to resting the transformed plant cells and prior to regeneration but selection may also be performed concurrently or subsequent to another step, e.g. regeneration. In some cases, the resting step is omitted and selection may be performed immediately subsequent to introduction of the nucleic acid, e.g. for electroporation, or particle bombardment or *Agrobacterium* infection. "Selecting" as used herein refers to the culture step in plant transformation where the transformed cells that have received and are expressing a selection marker from the introduced nucleic acid are selected. In some cases, cells may be exposed to a selective pressure in order to favor those cells that express the selection marker and may include the use of a selective agent that allows for selection of transformants containing at least one selection marker insert. Any suitable selection marker may be used, and includes but is not limited to bar, pat, GAT, PMI, hpt, nptII and positive and/or negative selectable markers and visible selection marker genes such as DS-RED, GFP, YFP, GUS and the like. Any suitable selective agent may be used, and includes but is not limited to herbicides, such as, bialaphos, glufosinate-NH4 (PPT), sugar, such as mannose, and antibiotics such as hygromycin B or G418, and the like.

Any suitable selection media may be used so long it allows expression of the selection marker. Exemplary selection media include without limitation DBC1, DBC2, DBC3, PHI-U and the like. In one aspect, the selection media includes media having copper, an auxin, a cytokinin or combinations thereof. Suitable forms of copper, auxins, and cytokinins for use in the media are described elsewhere herein.

In one aspect, copper is present in the selection medium at concentrations from about 0.1 µM to about 50 µM, preferably equal to or greater than 5 µM. In one embodiment, the selection medium has about 1 µM, 2 µM, 3 µM, 4 µM, 5 µM, 10 µM, 15 µM, 20 µM, 25 µM, 30 µM, 35 µM, 40 µM, 45 µM, 50 µM or greater concentration of copper. In one embodiment, the selection medium comprises from about 1.0 µM to about 5.0 µM of copper, for example, 1 µM, 2 µM, 3 µM, 4 µM, 5 µM or greater. Preferably, cupric sulfate is utilized. Typically the selection medium includes antibiotics, for example, embryos may be transferred to plates having a solid medium containing the carbenicillin for selection. Accordingly, in one aspect, the selection medium includes DCB3 media and an antibiotic to retard growth of *Agrobacterium*. In one embodiment, the selection medium includes DBC3 media and may also include an additive of antibiotics, such as carbenicillin at 100 to 150 mg/L and the like.

Auxins may be added to the selection medium and include, but are not limited to 2,4-dichlorophenoxyacetic acid (2,4-D), dicamba, naphthaleneacetic acid (NAA), indoleacetic acid (IAA), picloram, 2,4,5-trichlorophenoxyacetic acid, 4-chloro-indoleacetic acid, phenylacetic acid (PAA) or indole-3-butyric acid (IBA) and the like and combinations thereof. The selection medium may include one or more auxins, such as 2,4-D, in an amount of up to about 0.01 mg/L to about 10 mg/L, preferably from about 0.01 mg/L to about 5 mg/L. In one embodiment, when selecting monocot plant cells on a medium, the auxin such as 2,4-D is present in the selection medium is at concentrations of about 0.1 mg/L, 0.2 mg/L, 0.3 mg/L, 0.4 mg/L, 0.5 mg/L, 1.0 mg/L, 2.0 mg/L, 3.0 mg/L, 4.0 mg/L or 5.0 mg/L, 6.0 mg/L, 7.0 mg/L, 8.0 mg/L, 9.0 mg/L or 10.0 mg/L or greater. One example of an auxin for use in the methods is 1.0 mg/L to 2.0 mg/L of 2,4-D. See Examples 1-2. Other auxins having a different concentration may be used in the selection medium.

In a preferred embodiment, the cytokinin, e.g. BAP, is present in the selection medium from about 0.01 mg/L to about 0.5 mg/L. The selection medium may have about 0.01 mg/L, 0.1 mg/L, 0.2 mg/L, 0.3 mg/L, 0.4 mg/L, 0.5 mg/L, or greater of a cytokinin, e.g. BAP. More preferably, about 0.5 mg/L of BAP is present in the selection medium. In a preferred embodiment, a cytokinin, for example, BAP is present in the selection medium, preferably from about 0.01 mg/L of BAP in DBC1 medium or 0.5 mg/L BAP in DBC3 medium.

Selecting may optionally be carried out in light, dim or dark conditions. The length of exposure of the plant cell to light, dim or dark conditions may vary based in part on the type of plant species and genotype being transformed. For example, using the methods described herein, the selection step of transforming maize plant cells may take about 6 to about 16 weeks, typically about 6 to about 12 weeks, whereas the selection step for transforming sorghum plant cells is about 2 to about 3 or 4 months. Preferably, plant cells are rested and selected in dark conditions. As demonstrated in Examples 10-13, this combination leads to increased transformation frequency and efficiency in sorghum and corn. Alternately, the resting and selecting steps may be performed in dim conditions (Example 9) or in alternating dim and dark conditions (Example 1 and 10).

In a preferred embodiment, culturing in dark conditions may produce non-green tissue for use in regenerating the tissue into a plant. As used herein, "non-green tissue" is shiny, nodular but not green to the naked eye, which is in contrast to green tissue or green callus that is green, shiny, nodular and compact tissue that is produced by exposure to light. See U.S. Pat. No. 7,102,056, incorporated by reference in its entirety. Exemplary non-green tissues include but are not limited to callus, embryo, and organogenic tissues, such as Type I callus, meristematic tissues and the like. A preferred method of increasing transformation frequency and efficiency includes co-cultivating *Agrobacterium*-infected plant cells on PHI-T media and then, in at least one of the resting and selection steps, having the cells on DBC3 medium. This combined media system is described in further detail below.

The methods provide for an efficient method of increasing the transformation of monocots. Any suitable monocot may be used in the methods and systems described herein. These include without limitation, rice, barley, wheat, maize, sorghum, rye, oat, triticale, sugarcane, orchardgrass, tall fescue, red fescue, creeping bent grass, Kentucky bluegrass, perennial ryegrass, switchgrass, *Miscanthus* and the like. Preferably, the monocots are maize or sorghum. Advantageously, use of these methods shortens the time needed to perform the selecting or regenerating steps or preferably both. This time reduction may be achieved through the synergy of using a combined media system in conjunction with culturing the transformed cells in light, dim or dark conditions, preferably in dark conditions in one or more of the culturing steps, e.g. co-cultivating, resting, or selecting the transformed cells, as described elsewhere herein.

In one embodiment of the invention, the method includes the use of a combined media system in the co-cultivating, resting and selecting steps. Use of the combined media system includes co-cultivating *Agrobacterium*-infected plant cells in light, dim, or dark conditions on a co-cultivation medium that includes a low concentration of copper and an auxin and resting the plant cell on a resting medium that includes copper, an auxin, and a cytokinin. As used herein, the term "low concentration" includes copper that is in the medium or added to the medium so that the medium has about 0.1 µM or less than 0.1 µM total concentration. Preferably, about 1 mg/L to about 2 mg/L of an auxin, e.g. 2,4-D, and about 0.1 µM of copper, e.g. cupric sulfate, is in the co-cultivation medium of the combined media system. The resting and selecting media of the combined media system typically include about 0.1 mg/L, 0.2 mg/L, 0.3 mg/L, or 0.4 mg/L, 0.5 mg/L or greater amount of a cytokinin, e.g. BAP, and about 1 µM, 2 µM, 3 µM, 4 µM, 5 µM or greater concentration of copper, e.g. cupric sulfate.

In one embodiment, the combined media system includes a co-cultivation medium of PHI-T medium, a resting medium of DBC3 medium, and a selection medium of DBC3 medium. PHI-T medium includes 2,4-D and copper, typically about 2.0 mg/L of 2,4-D and about 0.1 µM copper respectively. DBC3 medium typically includes 1.0 mg/L 2,4-D, 0.5 mg/L BAP, and 5.0 µM cupric sulfate, including 0.1 µM from MS salts. Additional components of the PHI-T and DBC3 media are described elsewhere herein. See Example 1. In a preferred embodiment, the resting medium, e.g. DBC3 medium, also includes antibiotics capable of inhibiting the growth of *Agrobacterium*. As will be apparent to one skilled in the art, when non-*Agrobacterium*-mediated transformation methods are used to introduce the nucleic acid into plant cells, e.g. electroporation or particle bombardment, the combined media system may used to culture the transformed plant cells. For example, the transformed plant cell may be cultured on the co-cultivation medium and then subsequently cultured or subcultured on the resting medium and/or selection medium.

As disclosed herein and demonstrated in Examples 9 and 11, this combined media system results in increased transformation frequency. Unexpectedly, the combined media system and methods of the invention provide environmental conditions so that the transformed maize and sorghum plant cells and resulting tissue have higher frequencies of callus initiation by as much as 30% and 55% respectively than use of the same medium for both co-cultivating and resting steps. See Examples 7 and 12. Not only are a greater quantity of calli produced but the resulting calli are also of a much higher quality. See Examples 7 and 12 herein. As demonstrated in Example 11, the system and methods succeeded in increasing the percentage of callus transformed and notably stably transforming sorghum plants when conventional Type I callus media did not. The calli produced have increased transformation frequency/efficiency of monocots compared to conventional methods. In maize, plants are regenerated at higher frequencies on the average by as much as 20%. See Example 9. In sorghum, the average transformation frequency doubled. See Example 11. Accordingly, methods for increasing callus transformation frequency, callus initiation frequency, increasing or improving the quality of callus, and increasing the stable transformation of monocots, in particular maize and sorghum are provided.

In general, transformation frequency is increased by at least 3%, 5%, 7%, 8%, 9%, 10%, 11%, 12%, 13%, 14%, 15%, 20%, 30%, 40% and preferably 50%, 60%, 70%, 80%, 90% or 100% greater than the transformation frequency relative to a control. The "control" provides a reference point for measuring changes in phenotype of the subject plant or plant cell, e.g. transformation frequency/efficiency, callus quality or transformation process time. The control may comprise, for example: plant cells, i.e., transformed plant cells, which are not exposed to certain conditions (e.g. culture media or additive in the culture media) or certain stimuli (light, dark, or dim conditions) as the subject.

The frequency of transformed plant cells achieved using these methods may be evaluated using any suitable method or technique, for example, molecular analysis. See Example 3 herein. Putative transgenic events may be analyzed to confirm their transgenic nature. The choice of specific analytical test performed on any transgenic is dependent on the transgene. In general, almost all events are tested for the presence of the gene of interest by PCR or the transgene product (protein) can also be assayed. For example, in those events produced with the GUS gene, tissues are stained with GUS histochemical assay reagent. Additionally, T0 plants can also be painted with bialaphos herbicide (1% v/v Liberty) if these plants were transformed with bar or pat gene. The subsequent lack of herbicide-injury lesion indicates the presence and action of the BAR/PAT transgene product, which conditions for herbicide resistance. Southern blotting may be utilized to determine copy number, insertion pattern, rearrangement and integration vector backbone DNA into the genome. For example, when using a visible marker such as RFP, transformation frequencies may be determined by counting the numbers of embryos with large multicellular RFP positive cells clusters using a RFP microscope, and representing these as a percentage of the original number of embryos bombarded. See also Example 8. Thus, the varying media and darkness conditions or the combined media system may be readily evaluated for their ability to increase transformation frequencies over the control treatment.

As mentioned above and demonstrated in the Examples section, increasing transformation frequency may have effects throughout the whole transformation process including increasing callus transformation frequency and increasing plant transformation efficiency. See Examples 11-12.

E. Regenerating the Transformed Plant Cells

Provided herein are methods for increasing the efficiency of monocot plant transformation. The methods can be used for transformation and regeneration of plant species including, but not limited to, rice, barley, wheat, maize, sorghum, rye, oat, triticale, sugarcane, orchardgrass, tall fescue, red fescue, creeping bentgrass, Kentucky bluegrass, perennial ryegrass, switchgrass, *Miscanthus* and the like. While any sorghum line or variety can be used in the transformation methods, examples of sorghum lines include but are not limited to public lines such as CS3541, M91051, SRN39, Shanqui red, IS8260, IS4225, Tx430, P898012, P954035, PP290 (Casas et al. supra) and commercially important Pioneer proprietary inbred lines such as PH860, PH987, PHB180, PHB123, and PHB82.

As described above and in the examples below, the methods includes introducing the nucleic acid into the plant cell of the explant to produce a transformed plant cell and culturing the transformed plant cell on media including copper and an auxin and optionally a cytokinin to produce transformed tissue. To regenerate a plant, the method further includes selecting transformed tissue so that it may be regenerated into a plant using standard methods known to one skilled in the art or those described elsewhere herein. The method may include regenerating the transformed tissue on a regeneration media to produce a transformed plant. "Regenerating" as used herein refers to regenerating transformed plant cells or tissues into a plant. This step occurs after the culturing of transformed cells, which may include some or all of the steps of *Agrobacterium*-infection, preculturing, co-cultivating, resting and selecting depending on the transformation technique used to deliver the transgene, e.g. *Agrobacterium*-mediated, electroporation, or particle bombardment techniques. The methods may further include regenerating transformed plant cells into a plant by culturing the transformed cells on regeneration medium in light, dim, or dark conditions for several weeks, e.g. about 1 to 3 weeks. Preferably, transformed maize and sorghum plant cells are regenerated in dark conditions. Preferred regeneration media include media, such as PHI-RF media, as provided in the Examples. Methods for plant regeneration are known in the art. See, for example, Kamo et al. (Bot. Gaz 146(3):327-334, 1985), West et al. (The Plant Cell 5:1361-1369, 1993), and Duncan et al. (Planta 165:322-332, 1985), herein incorporated by reference in its entirety.

F. Rooting

Depending on the species of the plant cell being regenerated, the calli may be cultured on rooting medium in light conditions or a light/dark cycle. Any rooting medium that allows for the growth of shoots or roots may be employed, such as PHI-Z and PHI-RR. For example, with respect to sorghum, the calli may be cultured on rooting medium of PHI-Z in a light/dark cycle until shoots and roots develop. The appropriate duration of exposure to a rooting medium and light is known to one skilled in the art. Small plantlets are then transferred to tubes containing rooting medium and allowed to grow and develop more roots for approximately another week. The plants are then transplanted to soil mixture in pots in the greenhouse.

Accordingly, use of the combined media system or the methods described herein or combinations thereof produces a transformed tissue which is regenerated to produce a transformed plant in less time than usual. Surprisingly, using the methods or combined media system described herein allows one to transform and regenerate a sorghum plant in about the same time it normally takes to select for transformed callus tissue, which is on the average about six to eight months.

Furthermore, this method provides for the regeneration of a transformed plant from a plant species known to be recalcitrant for transformation, such as sorghum, in less than or about 5 months from the time of introducing the nucleic acid into the plant cell. As used herein, recalcitrant also refers to tissues or genotypes normally not amenable to culture. The regeneration of a transformed plant may be shortened by about 3 months as compared to results achieved using standard transformation techniques. In another aspect, the method of increasing transformation efficiency includes selecting for transformed plant cells in a period of time of 3 months or less, in particular with respect to a recalcitrant species such as sorghum. In another aspect, the method of increasing transformation efficiency includes regenerating a transformed plant cell into a plant in a period of time of about 3-10 weeks, preferably 3 weeks or less. As shown in Example 13, the selection and regeneration steps may be shortened by as much as 2 months and 5 weeks respectively. Accordingly, the overall transformation efficiency process was increased by at least 1.5 fold compared to standard methods that utilize standard callus induction media and individual steps in this process, e.g. selecting and regenerating were found to be increased by at least 1.5 or 2.5 fold.

The selected transformed cells, tissue, callus and/or non-green tissue may be subjected to a regeneration medium for regenerating transformed cells into plants. For example, the callus may be transferred to plates having a solid regeneration medium. Any suitable regeneration media may be used so long as it allows for the growth of the transformed plant cells, tissue, callus and/or shoot development. Exemplary regeneration media include but are not limited to PHI-RF, PHI-Z, PHI-RR and the like. See Examples 1 and 2. After shoot development, tissue can be transferred to a rooting medium, including but not limited to PHI-Z or PHI-RR. See Example 1 and 2.

In general, transformation efficiency is increased by at least 3%, 5%, 7%, 8%, 9%, 10%, 11%, 12%, 13%, 14%, 15%, 20%, 30%, 40% and preferably 50%, 60%, 70%, 80%, 90% or 100% greater than the transformation efficiency relative to a control. The "control" provides a reference point for measuring changes in phenotype of the subject plant or plant cell, e.g. transformation frequency/efficiency, growth rate and embryogenic character of transgenic calli, the time needed to recover regenerable calli, and/or the time needed to regenerate vigorous fertile plants. The control may comprise, for example, plant cells, i.e., transformed plant cells, which are not exposed to certain conditions (e.g. culture media or additive in the culture media) or certain stimuli (light, dark, or dim conditions) as the subject. The transformation efficiency may be observed by any suitable means as known to one skilled in the art and as described herein. For example, efficiency may be evaluated as the number of explants that generate transgenic events divided by the number of explants infected by *Agrobacterium* or bombarded by particle gun. This method also relates to maize plants transformed by this method and to maize cells transformed by this method.

Advantageously, methods of the invention and combined media system may used to increase transformation frequency, increase callus initiation frequency, increase the growth rate and embryogenic character of calli, e.g. transgenic or non-transgenic callus, reduce the time needed to recover regenerable calli, and make regeneration of vigorous fertile plants easier and more reproducible or any combination of these. As used herein, "callus initiation frequency" refers to the number of embryos that initiate callus tissue formation divided by the number of initial embryo targets. Callus induction as used herein refers to the tissue culture techniques and methods, such as media, culture conditions, and explants etc. used to induce callus initiation. Callus initiation refers to the callus starting to form from the cultured explants induced by the callus induction techniques and methods.

A method of increasing callus initiation frequency includes culturing a monocot plant cell of an explant on a cell culture medium comprising copper and an auxin. Any suitable explant from a monocot plant may be used and exemplary explants and monocot plants are described elsewhere herein. The monocot plant cell may be transgenic or non-transgenic. Accordingly, in some examples, the method includes introducing a nucleic acid into the monocot plant cell prior to, concomitant with, or subsequent to culturing the plant cell in the cell culture medium. Generally, the cell culture medium comprises copper, an auxin, and optionally a cytokinin. Suitable forms of copper, auxins, and cytokinins for use in the media are described elsewhere herein. The first cell culture medium includes about 0.1 µM to about 50 µM of copper and about 0.1 mg/L to about 5 mg/L. Preferably, the copper concentration in the cell culture medium is about 0.1 µM copper or less. The cell culture medium generally excludes cytokinins; however, optionally, the medium may include a concentration of cytokinin from about 0.01 mg/L to about 5 mg/L. In one aspect, the cell culture medium is the co-cultivation medium described elsewhere herein. The plant cell may be subjected to light, dim or dark conditions for a suitable length of time for cell division and callus initiation to occur. Generally, the length of time is about 1 week to about 2 to 3 weeks.

The plant cell may be cultured on a second different cell culture medium comprising copper, an auxin, and a cytokinin under suitable conditions and for a sufficient amount of time to produce tissue. The second cell culture medium includes about 1 µM to about 50 µM of copper, about 0.1 mg/L to about 5 mg/L of auxin, and about 0.1 mg/L to about 5mg/L of cytokinin. In one aspect, the cell culture medium is the resting medium described elsewhere herein. The suitable conditions may include light, dim or dark conditions. In some examples, use of the methods increase callus initiation frequency as compared to a control, e.g. callus produced from an explant of an immature embryo that is not cultured on the first and second cell culture media.

In general, callus initiation frequency is increased by at least 3%, 5%, 7%, 8%, 9%, 10%, 11%, 12%, 13%, 14%, 15%, 20%, 30%, 40% and preferably 50%, 60%, 70%, 80%, 90% or 100% greater than the callus initiation frequency relative to a control, e.g. callus produced from an explant of an immature embryo that is not cultured on the first and second cell culture media or certain stimuli (light, dim or dark conditions) as the subject.

The callus produced using the methods and media described herein may be transformed. Transgenic plant cells or transformed tissue expressing the introduced nucleic acid may be selected on a selection medium. Appropriate selection media are described elsewhere herein. The transformed tissue expressing the introduced nucleic acid may be regenerated into a plant.

The callus produced using the methods described herein may be evaluated for increased or improved callus quality. Callus quality as used herein refers to the relative health and amount of growing, embryogenic tissue or regenerable tissue. Callus would be of high quality or improved quality if, by visual observation, the callus looked fresh, healthy, friable or/and fast growing with embryogenic structures and of low callus quality if it did not exhibit as many of these characteristics. Calli's quality may also be assessed a) using a scoring method, for example, scoring calluses as 0=non-embryogenic callus, 1=25% of the callus surface is embryogenic, 2=26-50% of the callus surface is embryogenic, 3=51-75% of the callus surface is embryogenic, 4=76-100% of the callus surface is embryogenic, and b) determining calli quality expressed in percentage as the number of as the number of embryogenic calluses/total number of calluses (scutella or inflorescence) assessed. Calluses with scores of 3 or 4 are considered to be of good quality. Callus quality may be determined using any suitable method, including for example, observing color and morphology changes in the callus tissue. See, for example, U.S. Pat. No. 6,541,257, herein incorporated by reference in its entirety. Callus growth may be determined using any suitable method, including for example, measuring the changes in weight of the callus tissue over time divided by the weight of the tissue as initially plated and the number of days cultured. See, for example, U.S. Pat. No. 6,541,257, herein incorporated by reference in its entirety.

All publications cited in this application are herein incorporated by reference to the same extent as if each individual publication or patent application was specifically and individually indicated to be incorporated by reference.

The invention will be further described by reference to the following detailed examples. It is understood, however, that there are many extensions, variations, and modifications on the basic theme of the invention beyond that shown in the examples and description, which are within the spirit and scope of the invention.

Example 1

Maize *Agrobacterium* Transformation Protocol

Immature embryos are the target explants for transformation. Source ears can be derived from maize plants grown under greenhouse, growth chamber, or field conditions. Immature ears are harvested 9-13 days post-pollination depending on growing conditions. The size of the immature embryos used in the transformation is ranged from 0.8 to 2.5 mm in length.

Immature ears are immersed in 10%-50% commercial bleach mixed with or without 1% Tween-20 for 10-30 min. under house vacuum. Subsequently, ears are rinsed with sterile water for 3 times and immature embryos are isolated for *Agrobacterium* infection.

Media for *Agrobacterium* Preparation Includes

Minimal AB an of 50 mL/L stock A, 50 mL/L stock B, 5 g/L glucose, 9 g/L Phytagar and antibiotic at appropriate concentration. Stock A includes 60 g/L $K_2HPO_4$, 20 g/L $NaH_2PO_4$, pH 7.0. Stock B includes 20 g/L $NH_4Cl$, 6 g/L $MgSO_4$ $7H_2O$, 3 g/L KCl, 0.2 g/L $CaCl_2$, 0.5 g/L $FeSO_4$ $H_2O$.

YP medium includes 5 g/L yeast extract, 10 g/L peptone, 5 g/L NaCl, 15 g/L Bacto-agar, antibiotic at appropriate concentration (Ishida, Y., Saito, H., Ohta, S., Hiei, Y., Komari, T., and Kumashiro, T. (1996) High efficiency transformation of maize (*Zea mays* L.) mediated by *Agrobacterium tumefaciens*. Nat. Biotechnol. 14, 745-750.)

Media for Plant Transformation

A. Stock Solutions 0.1 M acetosyringone Stock is prepared by dissolving 490 mg 3',5'-dimethoxy-4'-hydroxyacetophenone (Aldrich D13, 440-6) in 25 ml DMSO, filter sterilize, and freezing in 1 ml aliquots.

Bialaphos stock contains Herbiace herbicide obtained from Meiji Seika K. K., Japan and contains 20% active ingredient, bialaphos. A 20 ml of Herbiace is mixed with 80 ml DI water. A BAKERBOND spe column (VWR JT7020-13) is prepared by adding 1.5-2 mL absolute MeOH to each of 12 columns held in a column processor and collecting samples with Falcon 15 ml tubes (VWR21008-935), verifying that columns are empty of methanol (no drips); then flushing each column with 2-2.5 ml DI water, removing Falcon tubes and replacing with fresh tubes. 2 ml of Herbiace dilution is added to each of the conditioned columns; in the absence of a vacuum. When the green front of the herbicide reaches the fritted disk, the stopcock is turned off. The eluates from columns are combined and the bialaphos fraction in the tubes should be straw colored. Bialaphos concentration is determined by sampling 5 µl of eluate and diluting with 1995 µl DI water (1:400 dilution), measuring OD at 205 and 280 nm and computing bialaphos concentration with formula $E=27+120$ (OD280/OD205) in mg/ml and multiplying by 400 for the original concentration. Bialaphos frozen is stored. Bialaphos is diluted to 1 mg/ml for use in media and store in refrigerator no longer than 2 months.

B. Media

PHI-I is 4.3 g/L MS salts (GIBCO BRL catalog no. 11117-874), 0.5 mg/L nicotinic acid, 0.5 mg/L pyridoxine HCl, 1 mg/L thiamine HCl, 0.1 g/L myo-inositol, 1 g/L vitamin assay casamino acids, 1.5 mg/L 2,4-D, 68.5 g/L sucrose, 36 g/L glucose, pH 5.2. Add 100 µM acetosyringone is added before using.

PHI-T is PHI-I with reducing sucrose to 20 g/L and glucose to 10 g/L, increasing 2,4-D to 2 mg/L, adding 0.5 g/L MES buffer, 0.7 g/L L-proline, 10 mg/L ascorbic acid, 10 µM acetosyringone and 8 g/L agar, pH 5.8. PHI-T medium contains 0.1 uM copper in MS salts 4.3 mg/L, nicotinic acid 0.5 mg/L, pyridoxine HCl 0.5 mg/L, thiamine HCl 1 mg/L, myo-inositol 100 mg/L, 2,4-D 2 mg/L, sucrose 20 g/L, glucose 10 g/L, L-proline 700 mg/L, MES 0.5 g/L, acetosyringone 100 µM, ascorbic acid 10 mg/L and agar 8.0 g/L.

PHI-RF is 4.3 g/L MS salts (GIBCO BRL 11117-074) plus 0.5 mg/L nicotinic acid, 0.1 mg/L thiamine HCl, 0.5 mg/L pyridoxine HCl, 2.0 mg/L glycine, 0.1 g/L myo-inositol, 0.4 µM cupric sulfate, 0.5 mg/L zeatin (Sigma Z-0164), 1 mg/L IAA, 26.4 µg/L ABA, thidiazuron 0.1 mg/L, 60 g/L sucrose, 3 mg/L bialaphos, 100 mg/L carbenicillin, 8 g/L agar, pH 5.6.

PHI-RR is 4.3 g/L MS salts (GIBCO BRL catalog no. 11117-874), 5 mL/L MS vitamin mix, 40 g/L sucrose, 6 g/L agar, pH 5.6

DBC1 contains MS salts (4.3 g/L) plus maltose (30 g/L); thiamine-HCl (10 mL/L (0.1 mg/mL); myo-inositol (0.25 g/L); N-Z-amine-A (1 g/L)(casein Hydrolysate); proline (0.69 g/L); CuSO4 (4.9 µM); 2,4-D (2.0 mg/L); BAP (0.01 mg/L); Adjust volume to 1 L with ddH2O; pH 5.8—Adjust pH with 1 M KOH; Phytagel (3.5 g/L); autoclave.

DBC2 contains MS salts (4.3 g/L) plus maltose (30 g/L); thiamine-HCl (10 mL/L (0.2 mg/mL); myo-inositol (0.25 g/L); N-Z-amine-A (1 g/L) (casein hydrolysate); proline (0.69 g/L); CuSO4 (4.9 µM); 2,4-D (2.0 mg/L); BAP (0.1 mg/L); Adjust volume to 1 L with ddH2O; pH 5.8—Adjust pH with 1 M KOH; Phytagel (3.5 g/L); autoclave.

DBC3 contains MS salts (4.3 g/L) plus maltose (30 g/L); thiamine-HCl (10 mL/L (0.2 mg/mL); myo-inositol (0.25 g/L); N-Z-amine-A (1 g/L) (casein hydrolysate); proline (0.69 g/L); CuSO4 (4.9 µM); 2,4-D (1.0 mg/L); BAP (0.5 mg/L); Adjust volume to 1 L with ddH2O; pH 5.8—Adjust pH with 1 M KOH; phytagel (3.5 g/L); autoclave.

*Agrobacterium* Strain and Vector

The engineered *Agrobacterium tumefaciens* in strain LBA4404 or EHA101/EH105, a binary vector contained a selectable marker gene, such as bar (Thompson, C., Movva, N. R., Tizard, R., Crameri, R., Davies, J. E., Lauwereys, M. and Botterman, J. (1987) Characterization of the herbicide-resistance gene bar from *streptomyces hygroscopicus*. EMBO J. 6:2519-2523.), or Pat (Wohlleben, W., Arnold W., Broer, I., Hillemann, D., Strauch, E., and Punier, A. (1988) Nucleotide sequence of the phosphinothricin N-acetyltransferase gene from *Streptomyces viridochromogenes* Tu494 and its expression in *Nicotiana tabacum*. Gene 70:25037) within the two borders of the T-DNA. Other marker genes, such as intron-DsRed (Fernando Rodrigues, Martijn van Hemert, H. Yde Steensma, Manuela Côrte-Real and Cecíla Leão, (2001) Red Fluorescent Protein (DsRed) as a Reporter in *Saccharomyces cerevisiae*. Journal of Bacteriology. 183 (12): 3791-3794; Keito Nishizawa, Yoichi Kita, Masahiko Kitayama, Masao Ishimoto, (2006), A red fluorescent protein, DsRed2, as a visual reporter for transient expression and stable transformation in soybean. Plant Cell Rep. 25:1355-1361:) or intron-GUS (Jefferson, R. A., Burgess, S. M., and Hirsh, D. (1986) β-Glucuronidase from *Escherichia coli* as a gene-fusion marker. Proc. Natl. Acad. Sci. USA 83:8447-8451; Vancanneyt, G., Schmidt, R., O'Connor-Sanchez, A., Willmitzer, L., and Rocha-Sosa, M. (1990) Construction of an intron-containing marker gene: Splicing of the intron in transgenic plants and its use in monitoring early events in *Agrobacterium*-mediated plant transformation. Mol Gen Genet. 220:245-250; Ohta, S., Mita, S., Hattori, T., and Nakamura, K. (1990) Construction and expression in tobacco of a β-glucuronidase (GUS) reporter gene containing an intron within the coding sequence. Plant Cell Physiol. 31:805-813) were also cloned within the T-DNA boarders.

*Agrobacterium tumefaciens* strains are stored as glycerol stocks at −70° C. Using standard microbiological technique, streak a loop-full of bacteria to produce single colonies on minimal AB medium in a 100×15 Petri dish and incubate the plate, inverted, at 28° C. in the dark for 2-3 days. Bacteria on a master plate are usable for up to 4 weeks if the plates are sealed with Parafilm and stored in the cold (4° C.).

From a master plate, pick 1-3 colonies to streak a fresh plate of YP medium. Incubate bacterial plate inverted, at 28° C., in darkness, for 1-3 days.

Preparation of Bacteria for Embryo Infection

PHI-I infection medium is warmed to room temperature. Bacteria off the working plate is scraped and placed in PHI-I medium with 100 μM acetosyringone. The medium is vigorously shaken and/or vortexed until clumps are broken up to form a uniform suspension as determined by visual inspection. One ml of *Agrobacterium*-suspension is used to determine optical density at 550 nm. If OD is over 1.0, dilute with PHI-I until OD is between 0.35 and 1.0. When the OD is between 0.35 and 1.0, the *Agrobacterium* suspension is diluted to OD 0.35 with PHI-I.

Immature Embryo Preparation

Aseptically dissect embryos from caryopses and place in a 2-ml microtube containing 2 ml PHI-I following standard methods for maize.

*Agrobacterium* Infection

One ml of PHI-I is removed and added to 1 ml *Agrobacterium* suspension. The tube is inverted to mix and incubated for minutes at room temperature.

Co-Cultivation

*Agrobacterium* suspension is removed from infection step with 1 ml micropipettor. The embryos are scraped from the tube using a sterile spatula. The immature embryos are transferred to plate of PHI-T medium in a 100×15 mm Petri dish. The embryos are oriented with embryonic axis down on the surface of the medium. The plates with embryos are cultured at 21° C., in darkness, for three days. Or the embryos also can be transferred to DBC1 plus 100 μM acetosyringone for co-cultivation with the same orientation, and incubated at 21° C. for 3 days. Alternatively, the embryos can be transferred to plates of DBC3 plus 100 μM acetosyringone for co-cultivation with the same orientation and incubated at 21° C. for 3 days.

Resting

Transfer embryos from co-cultivation medium to DBC3 medium plus 100 mg/L cabenicillin with the same embryo orientation and incubate at 28° C. in dark for 4 days.

Selection of Putative Transgenic Events

Ten embryos are transferred to each plate of DBC3 plus 3 mg/L bialaphos and 100 mg/L carbenicillin selection medium in a 100×15 mm Petri dish, maintaining orientation. Dishes are sealed with Parafilm. Plates are incubated in darkness or dim light at 28° C. Actively growing putative events, as pale yellow embryogenic tissue, should be visible in 6-8 weeks. Embryos that produce no events may be brown and necrotic, and little friable tissue growth is evident. Putative transgenic embryogenic tissue are submitted to fresh plates of DBC3 plus 3 mg/L bialaphos and 100 mg/L carbenicillin at 2-3 week intervals, depending on growth rate. Events are recorded.

Regeneration of $T_0$ Plants

Tissues are subcultured to regeneration medium PHI-RF, in 100×25 mm Petri dishes. Plates are incubated at 28° C., in darkness or dim light or normal light till shoots growing out for about 10 to 18 days. Shoots are transferred to rooting medium plates PHI-RR incubated at 28° C. in the light (about 80 vE μ−2 σεχ−1 from Cool White or equivalent fluorescent lamps) for 7-10 days. Individual plants are transferred to PHI-RR medium in 150×25 mm glass tubes covered with closures, and incubated at 28° C. in the light (about 80 vE μ−2 σεχ−1 from Cool White or equivalent fluorescent lamps). In 7-10 days, regenerated plants, about 10 cm tall, are potted in horticultural mix and hardened-off using standard horticultural methods.

Confirmation of Transformation

Putative transgenic events should be subjected to analyses to confirm their transgenic nature. The choice of specific analytical test performed on any transgenic is dependent on the transgene. In general, almost all events are tested for the presence of the gene of interest by PCR. Transgene product can also be assayed. For example, in those events produced with the GUS gene, tissues are stained with GUS histochemical assay reagent. Additionally, T0 plants can also be painted with bialaphos herbicide (1% v/v Liberty). The subsequent lack of herbicide-injury lesion indicates the presence and action of the BAR/PAT transgene product, which conditions for herbicide resistance. Usually, Southern blotting is used to determine copy number, insertion pattern, rearrangement and integration vector backbone DNA into maize genome (Zhao, Z Y., Gu, W., Cai, T., Tagliani, L. A., Hondred, D., Bond, D., Krell, S., Rudert, M. L., Bruce, W. B., and Pierce, D. A. (1998) Molecular analysis of $T_0$ plants transformed by *Agrobacterium* and comparison of *Agrobacterium*-mediated transformation with bombardment transformation in maize. Maize Genet. Coop. Newsl. 72, 34-37).

Example 2

Sorghum *Agrobacterium* Transformation Protocol

Use *Agrobacterium tumefaciens* LBA4404 and a super-binary vector constructed with pSB1 and pSB11 (Komari, T., Hiei, Y., Saito, Y., Murai, N. and Kumashiro, T. (1996) Vectors carrying two separate T-DNAs for co-transformation of higher plants mediated by *Agrobacterium tumefaciens* and segregation of transformants free from selection markers. Plant J. 10, 165-174; Thompson, C., Movva, N. R., Tizard, R., Crameri, R., Davies, J. E., Lauwereys, M., and Botterman, J. (1987) Characterization of the herbicide-resistance gene bar from *streptomyces hygroscopicus*. EMBO J. 6:2519-2523) for sorghum transformation. The super-binary vector contains a selectable marker gene, bar (Chalfie, M., Tu, Yuan, Euskirchen, G., Ward, W. W., and Prasher, D. C. (1994) Green fluorescent protein as a marker for gene expression. Science 263:802-805) and a visible marker gene, such as red fluorescent protein (RFP), yellow fluorescent protein (YFP), or intron-GFP (Jefferson, R. A., Burgess, S. M., and Hirsh, D. (1986) β-Glucuronidase from *Escherichia coli* as a gene-fusion marker. Proc. Natl. Acad. Sci. USA 83:8447-8451).

Media for *Agrobacterium* Preparation

Minimal AB includes 50 mL/L stock A, 50 mL/L stock B, 5 g/L glucose, 9 g/L Phytagar. For *Agrobacterium* strain used in this protocol, add 50 mg/L spectinomycin after autoclave. Stock A includes 60 g/L $K_2HPO_4$, 20 g/L $NaH_2PO_4$, pH 7.0. Stock B is 20 g/L $NH_4Cl$, 6 g/L $MgSO_4$ $7H_2O$, 3 g/L KCl, 0.2 g/L $CaCl_2$, 0.5 g/L $FeSO_4$ $H_2O$. YP medium is 5 g/L yeast extract, 10 g/L peptone, 5 g/L NaCl, 15 g/L Bacto-agar. For *Agrobacterium* stain used in this protocol, add 50 mg/L spectinomycin after autoclave.

Stock Solutions for Sorghum Transformation 0.1 M acetosyringone stock is prepared by dissolving 490 mg 3',5'-dimethoxy-4'-hydroxyacetophenone (Aldrich D13, 440-6) in 25 ml DMSO, filter sterilizing, and freezing at −20° C. in 1 ml aliquots. Bialaphos stock was prepared from herbicide, Herbiace® herbicide obtained from Meiji Seika K. K., Japan; containing 20% active ingredient, bialaphos. 20 ml Herbiace is mixed with 80 ml DI water. BAKERBOND spe column (VWR JT7020-13) is prepared by adding 1.5-2 ml absolute methanol to each of 12 columns held in a column processor and collecting samples with Falcon 15 ml tubes (VWR21008-935), verifying that columns are empty of methanol (no drips); then flushing each column with 2-2.5 ml DI water, removing Falcon tubes and replacing with fresh tubes; adding 2 ml of Herbiace dilution to each of the conditioned columns; in the absence of the vacuum. When the green front of the herbicide reaches the fritted disk, the stopcock is turned off. The elutes from columns are combined and the bialaphos fraction in the tubes should be straw colored. Bialaphos concentration is determined by sampling 5 µl of elute and diluting with 1995 µl DI water (1:400 dilution), measuring OD at 205 and 280 nm and computing bialaphos concentration with formula $E=27+120$ ($OD_{280}/OD_{205}$) in mg/ml; multiplying by 400 for the original concentration. The bialaphos is stored at −20° C. Bialaphos is diluted to 1 mg/ml for use in media and stored in refrigerator no longer than 2 months and filter sterilized before adding to media.

MS vitamins stock is prepared by dissolving 10 mg nicotinic acid, 10 mg pyridoxine HCl, 2 mg thiamine HCl and 40 mg glycine in 100 ml of DI water, filter sterilizing and storing in refrigerator.

Media for Sorghum Transformation

PHI-I includes 4.3 g/L MS salts (GIBCO BRL catalog no. 11117-874), 0.5 mg/L nicotinic acid, 0.5 mg/L pyridoxine HCl, 1 mg/L thiamine HC1, 0.1 g/L myo-inositol, 1 g/L vitamin assay casamino acids, 1.5 mg/L 2,4-D, 68.5 g/L sucrose, 36 g/L glucose, pH 5.2. 100 µM acetosyringone is added before using.

PHI-T includes PHI-I with reducing sucrose to 20 g/L and glucose to 10 g/L, increasing 2,4-D to 2 mg/L, adding 0.5 g/L MES buffer, 0.7 g/L L-proline, 10 mg/L ascorbic acid, 100 µM acetosyringone and 8 g/L agar, pH 5.8.

PHI-U includes PHI-T with 1.5 mg/L 2,4-D, 100 mg/L carbenicillin, 5 mg/L PPT (glufosinate-HN4), without glucose and acetosyringone.

PHI-RF includes 4.3 g/L MS salts (GIBCO BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.4 µM cupric sulfate, 0.5 mg/L zeatin (Sigma Z-0164), 1 mg/L IAA, 26.4 µg/L ABA, thidiazuron 0.1 mg/L, 60 g/L sucrose, 3 mg/L bialaphos, 100 mg/L carbenicillin, 8 g/L agar, pH 5.6.

PHI-Z includes 2.15 g/L MS salts, 2.5 mL/L MS vitamin mix, 20 g/L sucrose, 3 g/L gelrite pH 5.6

DBC3 media contains MS salts (4.3 g/L); maltose (30 g/L); thiamine-HCl (10 mL/L (0.2 mg/ml)); myo-inositol(0.25 g/L); N-Z-amine-A (1 g/L) (casein hydrolysate); proline (0.69 g/L); $CuSO_4$ (4.9 µM); 2,4-D (1.0 mg/L); BAP (0.5 mg/L); Adjust volume to 1 L with $ddH_2O$; pH 5.8—Adjust pH with 1 M KOH; phytagel (3.5 g/L); autoclave.

Preparation of *Agrobacterium*

Master plate is prepared by storing *Agrobacterium* strains as glycerol stocks at −70° C. Using standard microbiological technique, a loop-full of bacteria is streaked to produce single colonies on minimal AB medium in a 100×15 Petri dish and the plate incubated, inverted, at 28° C. in the dark for 2-3 days. Bacteria on a master plate are usable for up to 4 weeks if the plates are sealed with Parafilm and stored in the cold (4° C.).

Working plate is prepared by picking 2-3 colonies from a master plate and streaking a fresh plate of YP medium. The bacterial plate is incubated and inverted, at 28° C., in the dark, for 1-2 days.

Suspension for immature embryo infection includes adding acetosyringone to a certain volume of PHI-I medium (pre-warmed to room temperature) in a tube to make PHI-I with 100 µM acetosyringone. Bacteria is scraped off working plate with a sterile bacteria loop and placed in PHI-I with 100 µM acetosyringone. Vigorously vortexed to break clumps and form a uniform suspension as determined by visual inspection. 1 ml of agro-suspension is taken to measure optical density at 550 nm. The suspension is diluted with PHI-I plus 100 µM acetosyringone to $10^9$ cfu/mL (OD at 0.7).

Preparation of Immature Embryos

Sorghum plants are grown under greenhouse, growth chamber, or field conditions. Healthy sorghum plants are always important for success of transformation. Immature panicles are harvested 9-13 days post-pollination depending on the growing conditions. The size of immature zygotic embryos used in transformation is ranged from 0.8 to 2.5 mm in length. Immature kernels are taken off from the panicles and sterilized with 50% bleach and 0.1% Tween-20 for 30 min. with vacuum; then rinse the kernels with sterile water three times. The kernels are kept in sterile water before isolating embryos. Embryos are aseptically dissected from each sterilized sorghum kernel and place in a 2-ml microtube containing 2 ml PHI-I with 100 µl M acetosyringone. Usually, about 100 embryos are placed per tube, but it can be varied.

*Agrobacterium* Infection and Co-Cultivation of Embryos

PHI-I liquid is removed medium from the tube with 1 ml micropipettor and added to 1 ml *Agrobacterium* suspension. The tube is gently inverted a few times to mix well and incubated 5 minutes at room temperature. The *Agrobacterium* suspension is removed from the tube with 1 ml micropipettor. The embryos are scraped from the tube using a sterile spatula. Immature embryos are transferred to a plate of PHI-T medium in a 100×15 mm Petri dish. The embryos are oriented with embryonic axis down on the surface of the medium. These embryos are incubated at 21-25° C. in the dark for 3 days.

Resting

The embryos are transferred to DBC3 plus 100 mg/L carbenicillin or PHI-U minus PPT with the same embryos orientation and incubated at 28° C. in the dark for 4 days.

Selection of Putative Transgenic Events

The embryos are transferred to DBC3 plus 100 mg/L carbenicillin and 3 mg/L bialaphos or PHI-U medium and incubated at 28° C. in the dark for 2-3 weeks. Subcultured every two to three weeks for about 10-20 weeks to get enough callus for plants regeneration.

Regeneration of $T_o$ Plants

These calli are transferred to PHI-RF medium and incubated at 28° C. in the dark for approximately 2-3 weeks to develop shoots. When shoots form, move these cultures to a lighting culture room under conditions of 16 hours light (270

µE m$^{-2}$ sec$^{-1}$) and 8 hours dark at 25° C. Transfer shoots (about 3-5 cm tall) to plastic boxes (10×9×10 cm) containing PHI-Z medium. Culture these shoots under the same light and temperature conditions for 3-5 days. Each box contains shoots derived from a single embryo. When the plantlets reach about 8-10 cm tall with healthy roots, transfer these plantlets to pots with Universal Mix (Strong-Lite, Seneca, Ill. 61360) in greenhouse.

Example 3

Confirmation of Transformation

Analyze putative transgenic events to confirm T-DNA integration into the plant's genome. The choice of specific analytical methods performed on any transgenic is dependent on the transgene. In general, all events are assayed for the presence of the transgene by PCR or/and Southern blotting. The expression of the transgene(s) can also be assayed. For example, in the events produced with the GUS gene, tissues such as callus, leaf, roots, pollen and seeds etc., are stained with GUS histochemical assay reagent. If the events transformed with a bar gene, the transgenic plants can be painted with bialaphos herbicide (1% v/v Liberty). The subsequent lack of herbicide-injury lesion indicates the presence and expression of the bar transgene in these transgenic plants. Southern blotting is also used to determine the pattern of the integrated T-DNA, such as copy number, truncation and rearrangement etc.

Confirmation of transformation: To demonstrate stable transformation, the confirmation of the presence of the transgene(s) in the plant's genome should be at least in two generations, $T_0$ and $T_1$ by Southern blotting.

With *Agrobacterium*-mediated transformation, one of the important issues is the integration of the T-DNA vector backbone sequence into the plant's genome (Zhao, Z. Y., Gu, W., Cai, T., Tagliani, L., Hondred, D., Bond, D., Schroeder, S., Rudert, M., and Pierce D. (2001) High throughput genetic transformation mediated by *Agrobacterium tumefaciens* in maize. Molec. Breeding 8:323-333; Buck, S. D., Wilde, C. D., Montagou, M. V., and Depicker, A. (2000) T-DNA vector backbone sequences are frequently integrated into the genome of transgenic plants obtained by *Agrobacterium*-mediated transformation. Molec. Breeding 6:459-468; Wohlleben, W., Arnold, W., Broer, I., Hillemann, D., Strauch, E., and Punier, A. (1988) Nucleotide sequence of the phosphinothricin N-acetyltransferase gene from *Streptomyces viridochromogenes* Tu494 and its expression in *Nicotiana tabacum*. Gene 70:25-37). To elucidate the integration of the backbone sequence, Southern blotting or PCR assay against the vector backbone sequence should be performed.

Example 4

Culturing

*Agrobacterium* suspension for infection can also be prepared in liquid shake culture. One day prior to transformation, about 30 ml of minimal AB medium in a 30 ml baffle flask containing 50 µg/mL spectinomycin is inoculated with a ⅛ loop-full of *Agrobacterium* from a 1-2-day-old working plate. The *Agrobacterium* is grown at 28° C. at 200 rpm in the dark overnight (about 14 hours). In mid-log phase, the *Agrobacterium* cells are harvested and re-suspended at 10$^9$cfu/mL in PHI-I medium+100 µM acetosyringone using standard microbial techniques and standard curves. If 10$^9$ cfu/mL of *Agrobacterium* suspension causes serious damage of immature embryos of the genotype line, lower concentrations of *Agrobacterium* suspension should be tested. If the plant tissues produce more phenolic pigment, 1% polyvinylpolypyrrolidone (PVPP) can be added to co-cultivation medium PHI-T to protect plant tissues (Zhao, Z. Y., Glassman, K., Sewalt, V., Wang, N., Miller, M., Chang, S., Thommpson, T., Catron, S., Wu, E., Bidney, D., Kedebe, Y., and Jung, R. (2003) Nutritionally improved transgenic sorghum, in *Plant biotechnology* 2002 *and beyond, Proceedings of* 10$^{th}$ *IAPTC & B Congress* (Vasil, I. K., ed.) Kluwer Academic Publications, Dordrecht, Boston, London, pp. 413-416). In addition, PVPP can be added to the resting medium (PHI-T plus 100 mg/L carbenicillin and menus acetosyringone) and the selection medium (PHI-U and PHI-V) to protect callus growth.

L-cysteine can be used in the co-cultivation phase. Co-cultivation medium supplied with 100-400 mg/L L-cysteine may help for recovering stable transgenic events (Cheng, M., Fry, J. E., Pang, S., Zhou, H., Hironaka, C. M., Duncan, D. R., Conner, T. W., and Wan Y. (1997) Genetic transformation of wheat mediated by *Agrobacterium tumefaciens*. Plant Physiol. 115:971-980).

Example 5

Vectors

The vectors used herein are commonly used *Agrobacterium* transformation plasmid containing selectable or visual markers so that transformants can be identified or selected.

PHPMRFP contains the PAT gene under a 35S CAMV promoter and the maize Ubi promoter, first Ubi intron driving the DS-RED2INT visible marker gene. DS-RED2INT contains a plant intron (INT) which will not be expressed in the *Agrobacterium*, only expressed in the plant cells.

PHPMYFP contains the maize Ubi promoter and first Ubi intron driving the MO-PAT::ZS Yellow1-N1 gene. This is a fusion of mo-pat and yellow fluorescent protein (YFP).

PHPSRFP contains the maize Ubi promoter and first UBI intron driving the DS-RED2INT gene. DS-RED2INT contains a plant intron (INT) which will not be expressed in the *Agrobacterium*, only expressed in the plant cells.

Example 6

Transformation and Regeneration of Transgenic Maize Plants by Bombardment

Plant Material:

Plants of maize elite inbred line PHR03 are grown in the greenhouse or in the field under regular growing condition. Plants are either self-pollinated or sib-pollinated to produce immature ears. The immature embryos (9-13 DAP when embryo size around 0.8-2.5 mm) are isolated from sterilized ears and are placed on plates containing high osmotic media for 2-4 hours. High osmotic medium as used herein refers to the tissue culture medium containing high concentration of sucrose to protect explants from damage caused by bombardment. Typically the concentration of sucrose would range 12% -19% in the media and can be determined by one skilled in the art.

DNA Delivery by Particle Gun Bombardment:

Standard bombardment conditions are used to delivery the particle combined with plasmid DNA vector PHPMRFP.

Resting and Selection of Stable Transgenic Callus:

Following bombardment, the embryos are separately subcultured either on PHI-T medium or on DBC3 medium for 3 days (1-7 days) in dark without selection agent for resting and then sub-cultured on DBC3 medium with 3 mg/L biolophos for selection for 3 months in dark with medium changes every 2-3 weeks. The putative stable calli can be identified based on the visible marker gene (DSRED2INT Red fluorescent protein gene) expression. The callus transformation frequencies from different media in selection process can be calculated.

Transgenic Plant Regeneration and Confirmation:

All of these putative transgenic callus tissues are transferred to plant regeneration medium for plant regeneration under regular regeneration conditions. The final confirmation of stable transformation frequency is determined based on molecular analysis.

Example 7

Comparison of Combined Media System with DBC3 Medium for Callus Initiation and Callus Quality in Maize Immature embryos from maize inbred PHH9H were harvested 9-13 days post-pollination with embryo sizes ranging from 0.8-2.5 mm length and were co-cultivated on PHI-T medium for 3 days in dark conditions. These embryos were then transferred to DBC3 medium (described in U.S. Pat. No. 7,102,056) in dark conditions. The use of PHI-T medium and then DBC3 medium in cultures, respectively, comprises the Combined media system. A second set of immature embryos were isolated from the same ear as above and directly cultured on DBC3.

After 42 days of culturing on DBC3 medium or 39 days on the Combined media system, the callus initiation frequency and callus quality of these embryos were evaluated and compared (see Table 1). The immature embryos cultured in the Combined media system had higher frequencies of callus initiation (94%) than the embryos directly cultured on DBC3 medium (63%). In additional, the callus produced on the Combined media system was high quality callus while the callus produced on the DBC3 medium was low quality callus.

Callus induction as used herein refers to the tissue culture techniques and methods, such as media, culture conditions, and explants etc. used to induce callus initiation. Callus initiation as used herein refers to the callus starting to form from the cultured explants induced by the callus induction techniques and methods.

Callus quality as used herein refers to the relative health and amount of growing, embryogenic tissue or regenerable tissue. Callus would be of high quality if, by visual observation, it looked fresh, healthy, friable or/and fast growing with embryogenic structures and of low callus quality if it did not exhibit as many of these characteristics. Calli's quality may also be assessed using a scoring method, for example, scoring calli as 0=non-embryogenic callus, 1=25% of the callus surface is embryogenic, 2=25-50% of the callus surface is embryogenic, 3=50 75% of the callus surface is embryogenic, 4=75-100% of the callus surface is embryogenic, and b) determining calli quality expressed in percentage as the number of as the number of embryogenic calluses/total number of calluses (scutella or inflorescence) assessed. Calli with scores of 3 or 4 are considered to be of good quality.

These results show that the Combined media system protocol produced high callus induction frequency and that the callus quality was higher than when DBC3 medium was used.

TABLE 1

Comparison of Combined media system and the DBC3 medium on callus initiation frequency and callus quality

|  | Combined media system | DBC3 |
|---|---|---|
| Number of embryos in culture | 16 | 16 |
| Number of embryos producing callus | 15 (94%) | 10 (63%) |
| Callus quality | High quality | Low quality |

Example 8

Effects of Co-Cultivation Media on T-DNA Delivery and Embryo Survival

Maize inbred PHR03 immature embryos (9-13 DAP; embryo size around 0.8-2.5 mm) were infected with $5 \times 10^8$ cfu/mL Agrobacterium LBA4404 containing superbinary vector PHPMRFP in liquid medium PHI-I. The embryos were then cultured on one of two different Co-cultivation media plates at 21° C. in dark conditions for 3 days. These two Co-cultivation media were medium-1: PHI-T medium which contained 2,4-D only, no BAP; and medium-2: DBC1 (contained 2,4-D, 0.01 mg/L BAP and 5 µM copper, described in U.S. Pat. No. 7,102,056) plus 100 µM acetosyringone.

The T-DNA delivery efficiency and embryo survival frequency were evaluated at 6 days post Agrobacterium infection. The T-DNA delivery efficiency was measured as high, intermediate and low based on the number of the color spots due to expression of the visible marker gene (red fluorescent protein gene—RFP) on each of the infected embryos. Our observation was that embryo survival was based on whether the embryos begin to initiate growth of callus tissues and also on the health of these embryos. If an embryo was healthy with sectors of initial callus tissues, it survived after Agrobacterium infection. If an embryo shrank in size or turned to brown, it was dead after Agrobacterium infection. The results were listed in the table below. T-DNA delivery efficiency as used herein refers to the number of cells or cell clusters containing T-DNA as shown through a visible marker, referred as color spots or other method and compared the number of these color spots on each of the infected embryos, one can rate it as high (with a large number of color spots) intermediate (color spots between high and low) or low (with few of color spots) for T-DNA delivery. For example, if visual marker genes such as RFP, YFP or GFP are used as a marker of T-DNA delivery during transformation, the cells containing T-DNA will show the corresponding fluorescence protein. Embryo survival frequency as used herein refers to the number of embryos that initiate callus tissue formation divided by the number of initial embryo targets. This is also known as callus initiation frequency.

These experiments showed PHI-T medium for co-cultivation resulted in higher T-DNA delivery efficiency and better immature embryo survival frequency than DBC1 plus 100 µM acetosyringone. T-DNA delivery efficiency and high frequency of embryos survival following Agrobacterium infection were important for increasing transformation frequency.

TABLE 2

The T-DNA delivery efficiency and embryo survival frequency under different co-cultivating conditions in maize.

| | Co-cultivation media | | | |
|---|---|---|---|---|
| | PHI-T | | DBC1 + 100 μM acetosyringone | |
| Experiment | T-DNA delivery | Embryo survival frequency (%) | T-DNA delivery | Embryo survival frequency (%) |
| Exp. 1 | high | 100 | intermediate | 50 |
| Exp. 2 | high | 100 | intermediate | 50 |
| Exp. 3 | high | 100 | intermediate | 25 |
| Exp. 4 | high | 90 | intermediate | 5 |
| Exp. 5 | high | 90 | intermediate | 5 |
| Exp. 6 | high | 100 | intermediate | 15 |
| Exp. 7 | high | 100 | intermediate | 10 |
| Average | high | 97 | intermediate | 23 |

After the co-cultivation step, all of these embryos went through a resting step wherein they were all rested on the same medium (DBC3) in the same conditions. The resting step included culturing on medium DBC3 plus 100 mg/L carbenicillin under dim light (10-30 μE m$^{-2}$ sec$^{-1}$) at 28° C. for 3 days (this may range from 1-7 days).

After the resting step, all of these embryos went through a selection step on the same medium (DBC3) and in the same conditions. The selection step included culturing on medium DBC3 plus 100 mg/L carbenicillin and 3 mg/L bialaphos and under the dim light (10-30 μE m$^{-2}$ sec$^{-1}$) at 28° C. for about 7-8 weeks. The embryos were subcultured every 2-3 weeks.

A regeneration step is followed by culturing the putative transgenic callus on PHI-RF medium plates for producing shoots and a rooting step on medium plates PHI-RR.

Transformation frequency was calculated by the number of embryos producing transgenic plants divided by the number of embryos infected by *Agrobacterium*. (see Table 3)

The transformation frequency was highest with the Combined media system with PHI-T as the Co-cultivation medium and DBC3 as the resting and selection medium.

TABLE 3

Stable Transformation Frequency with Combined media system and 2 other media systems in maize

| | Combined media system | DBC1 & DBC3 | DBC3 |
|---|---|---|---|
| Co-cultivation media | PHI-T | DBC1 + 100 μM acetosyringone | DBC3 + 100 μM acetosyringone |
| Resting media | DBC3 + 100 mg/L carbenicillin | DBC3 + 100 mg/L carbenicillin | DBC3 + 100 mg/L carbenicillin |
| Selection media | DBC3 + 100 mg/L carbenicillin + 3 mg/L bialaphos | DBC3 + 100 mg/L carbenicillin + 3 mg/L bialaphos | DBC3 + 100 mg/L carbenicillin + 3 mg/L bialaphos |
| | Transformation Frequency (%) | | |
| Exp. 1 | 34.3 | 2.9 | 11.4 |
| Exp. 2 | 54.3 | 37.1 | 40 |
| Exp. 3 | 25.7 | 2.9 | 17.1 |
| Exp. 4 | 5.7 | 0 | 11.4 |
| Exp. 5 | 31.4 | 11.4 | 17.1 |
| Exp. 6 | 48.6 | 5.7 | 40 |
| Average | 33.3 | 10 | 22.9 |

Example 9

Combined Medium System giving High Transformation Frequency in Maize

Maize inbred PHR03 immature embryos (9-13 DAP when embryo size around 0.8-2.5 mm) were infected with 5×10$^8$ cfu/mL *Agrobacterium* LBA4404 containing superbinary vector PHPMRFP in PHI-I liquid medium. The embryos were then Co-cultivated on 3 different Co-cultivation media plates at 21° C. in dark conditions for 3 days. Alternatively, the co-cultivation in dark conditions may last from a time ranging from 1-7 days. These three Co-cultivation media were media #1 PHI-T medium; #2 DBC1 (described in U.S. Pat. No. 7,102,056) plus 100 μM acetosyringone and medium #3 DBC3 (described in U.S. Pat No. 7,102,056) plus 100 μM acetosyringone.

Example 10

Dark Condition Increases Transformation Frequency in Maize

In this example, culture media were identical for Trial #1 and Trial #2, however, the light conditions used in both the resting and selection steps varied between Trial #1 and Trial #2. Trial #1 was done in dim light conditions while Trial #2 was done in dark conditions. Maize inbred PHR03 immature embryos (9-13 DAP when embryo size around 0.8-2.5 mm) were infected with 5×10$^8$ cfu/mL *Agrobacterium* LBA4404 containing superbinary vector PHPMRFP in PHI-I liquid medium. The embryos were cultured on co-cultivation medium plates with PHI-T medium at 21° C. in dark conditions for 3 days (ranged 1-7 days).

The embryos were then randomly separated into two groups (Trial #1 and Trial #2) and were cultured on identical resting medium (DBC3+100 mg/L carbenicillin). In this resting step one group of the embryos was cultured in dim light (10-30 μE m$^{-2}$ sec$^{-1}$) (Trial #1) and another group of the embryos was cultured in dark (Trial #2) both for 3 days (range 0-7 days).

Embryos from each trial were then transferred to identical selection medium (DBC3+100 mg/L carbenicillin+3 mg/L bialaphos) and continued in their respective light conditions of Trial #1 in dim light or Trial #2 in dark conditions in the resting step. After two months from the initiation of the experiments, callus events were big enough for regeneration. Transformation frequency was calculated by the number of embryos producing transgenic plants divided by the number of embryos infected by *Agrobacterium* (see Table 4).

On average, the embryos from Trial #2 that both were rested and selected in dark conditions resulted in higher transformation frequencies (39.4%) than the embryos from Trial #1 that both were rested and selected in dim light (30.3%).

TABLE 4

Embryos from Trial #2 that both were rested and selected in dark conditions versus those rested and selected in dim light (Trial #1) Transformation Frequency (%)

| Trial | Trial #1 | Trial #2 |
|---|---|---|
| Co-cultivation | PHI-T & dark | PHI-T & dark |
| Resting | DBC3 + 100 mg/L carbenicillin & dim light | DBC3 + 100 mg/L carbenicillin & dark |
| Selection | DBC3 + 100 mg/L carbenicillin + 3 mg/L bialaphos & dim light | DBC3 + 100 mg/L carbenicillin + 3 mg/L bialaphos & dark |
| Expt. 1 | 40% | 36.7% |
| Expt. 2 | 2.9% | 31.4% |
| Expt. 3 | 37.1% | 60% |
| Expt. 4 | 37.1% | 37.1% |
| Expt. 5 | 14.3% | 5.7% |
| Expt. 6 | 37.1% | 74.3% |
| Expt. 7 | 45.7% | 57.1% |
| Expt. 8 | 17.1% | 11.4% |
| Expt. 9 | 42.9% | 40% |
| Average | 30.3% | 39.4% |

Example 11

Combined Medium System is Superior to Type I Callus Medium System in Sorghum Transformation Sorghum line TX430 immature embryos (9-15 DAP when embryo size around 0.8-2.5 mm) were infected with 1×10$^9$ cfu/mL *Agrobacterium* LBA4404 containing superbinary vector PHPMYFP in PHI-I liquid medium. The embryos were co-cultivated on PHI-T medium plates at 25° C. (ranged 21-25° C.) in dark for 3 days (ranged 1-7 days).

Then the embryos were transferred to 2 different resting conditions: Trial #1 DBC3+100 mg/L carbenicillin (U.S. Pat. No. 7,102,056); Trial #2 PHI-U (Type-1 callus medium) without PPT, both cultured in dark at 28° C. for 7 days (ranged 1-10 days).

These embryos were transferred to 2 different selection media: Trial #1 DBC3 (U.S. Pat No. 7,102,056)+100 mg/L carbenicillin+3 mg/L Bialaphos or Trial #2 PHI-U (Type-I callus medium). The whole selection step was in dark at 28° C. After two to three months from the initiation of the experiment, transgenic callus events were cultured for plant regeneration on the same regeneration medium (PHI-RF and PHI-Z) at the regular regeneration conditions.

The results showed that T0 plants were regenerated at higher frequencies when the Combined media system was used in Trial #1 than in Trial #2. Using the Combined media system as above also increased the percentage of transformed callus. Results also show that no stable transgenic plants were regenerated using PHI-T in the Co-cultivating and PHI-U media in both resting and selecting steps (Trial #2) (see Table 5). This result showed that the Combined media system was superior to the Type-I callus medium system for sorghum transformation.

These results indicated that stably transformed sorghum plants can be regenerated with both resting and selection in dark conditions using the Combined media system. These results indicated dim light is not needed in resting and selection steps in sorghum transformation.

TABLE 5

*Agrobacterium*-mediated sorghum transformation

| | Trial #1 Combined media system | | | Trial #2 Type I callus media system | | |
|---|---|---|---|---|---|---|
| Co-cultivation media | PHI-T | | | PHI-T | | |
| Resting media | DBC3 + 100 mg/L carbenicillin | | | PHI-U without PPT | | |
| Selection media | DBC3 + 100 mg/L carbenicillin + 3 mg/L Bialaphos | | | PHI-U | | |
| | # embryos infected | Callus transf. % | Plant Transf. % | # embryos infected | Callus transf. % | Plant Transf. % |
| Experiment | 20 | 10% | 10% | 20 | 5% | 0% |

Example 12

Combined Media System is Superior to DBC3 Media in Sorghum Transformation

Sorghum line TX430 immature embryos (9-15 DAP when embryo size around 0.8-2.5 mm) were infected with $1\times10^9$ cfu/mL *Agrobacterium* LBA4404 containing superbinary vector PHPSRFP in PHI-I liquid medium. The embryos were cultured on medium plates at 25° C. (ranged 21-25° C.) in dark for 3 days on 2 different co-cultivation media; Trial #1 PHI-T or Trial #2 DBC3 plus 100 µM acetosyringone. The embryos were transferred each to an identical medium, DBC3+100 mg/L carbenicillin for resting and were cultured in dark at 28° C. for 11 days (ranged 3-12 days). The embryos cultured with the Combined media system, Trial #1, were healthy and showed a higher callus initiation frequency after two weeks in culture. The embryos cultured on DBC3 medium, Trial #2 turned brown and had low to none callus initiation frequency.

TABLE 6

Sorghum callus initiation frequency in Combined media system and DBC3 medium

| | Trial #1 Combined media system | | Trial #2 DBC3 media | |
|---|---|---|---|---|
| Co-cultivation media | PHI-T | | DBC3 + 100 µM acetosyringone | |
| Resting media | DBC3 + 100 mg/L carbenicillin | | DBC3 + 100 mg/L carbenicillin | |
| | # embryos infected | # embryos-healthy & initiation callus (%) | # embryos infected | # embryos-healthy & initiation callus (%) |
| Exp. 1 | 47 | 24 (51%) | 46 | 3 (6.5%) |
| Exp. 2 | 39 | 15 (38%) | 40 | 4 (10%) |
| Exp. 3 | 40 | 28 (70%) | 40 | 0 (0%) |
| Exp. 4 | 39 | 39 (100%) | 37 | 1 (2.7%) |
| Sum (%) | 165 | 106 (62%) | 163 | 8 (5%) |

The results showed that callus initiation at higher frequencies when the Combined media system was used (Trial #1) than in Trial #2. Using the Combined media system as above also produced healthy callus tissues than DBC3 medium. The generation of high frequency of healthy calli following co-cultivation and resting is critical for increasing stable transformation frequency. This result showed that the Combined media system was superior to the DBC3 media for sorghum transformation. Also, these results confirmed dim light is not needed in co-cultivation and resting steps in sorghum transformation.

Example 13

Combined Medium System Speeding Up Sorghum Transformation Process

Sorghum line TX430 immature embryos (9-15 DAP when embryo size around 0.8-2.5 mm) were infected with $1\times10^9$ cfu/mL *Agrobacterium* LBA4404 containing superbinary vector PHPMYFP in PHI-I liquid medium. They were co-cultivated on PHI-T medium plates at 25° C. in dark for 3 days. Then the embryos were transferred to 2 medium systems, either Combined medium system (Trial #1) or Type I callus medium system (Trial #2) as used in Example 11.

These embryos were cultured on two different resting media: Trial #1 DBC3 plus 100 mg/L carbenicillin; Trial #2 PHI-U (Type-I callus medium) without PPT, both cultured in dark at 28° C. for 7 days (ranged 1-10 days). After 7 days, these embryos were transferred to 2 different selection media: Trial #1 DBC3 plus 100 mg/L carbenicillin and 3 mg/L Bialaphos or Trial #2 PHI-U. The whole selection step was in dark at 28° C. After two to three months from the initiation of the experiment, transgenic callus events were cultured for plant regeneration on the same regeneration medium, PHI-RF. After the regeneration step, shoots were transferred to rooting medium PHI-Z.

$T_0$ plants with strong shoots and roots were transplanted to soil in the greenhouse. The time spent from infection to $T_0$ plants to greenhouse in Trial #1 (5 months) was much shorter than that in Trial #2 (8 months) (see Table 7). These results showed that using Combined media system (Trial #1) increased efficiency of sorghum plant transformation. The selection time was reduced from 5 months (Trial #2) to 3 months (Trial #1), the regeneration time was reduced from 2 months or 8 weeks (Trial #2) to 3 weeks (Trial #1). These results also showed that using Combined media system (Trial #1) increased efficiency of the selecting and regeneration steps, speeded up the transformation process and reduced the transformation time frame from about 8 months to 5 months.

TABLE 7

Combined medium system speeding up the transformation process in sorghum

| | Trial | |
|---|---|---|
| | Trial #1 Combined medium system | Trial #2 Type I medium system |
| Cocultivation media | PHI-T | PHI-T |
| Resting media | DBC3 + 100 mg/L carbenicillin | PHI-U without PPT |
| Selection media | DBC3 + 100 mg/L carbenicillin + 3 mg/L Bialaphos | PHI-U |
| Regeneration media | PHI-RF | PHI-RF |
| Rooting media | PHI-Z | PHI-Z |
| Length on selection to get callus events ready for regeneration | 3 months | 5 months |
| Length on regeneration medium PHI-RF to get shoots | 3 weeks | 2 months |
| Length on rooting medium PHI-Z to get roots | 3 weeks | 3 weeks |
| Length from embryo infection to T0 plants to greenhouse | 5 months | 8 months |

Example 14

1 µM Copper and Above Increased Transformation Frequency in Maize

Maize inbred PHR03 immature embryos (9-13 DAP when embryo size around 0.8-2.5 mm) were infected with $5\times10^8$ cfu/mL *Agrobacterium* LBA4404 containing superbinary vector PHPMRFP in PHI-I liquid medium. The embryos were then co-cultivated on PHI-T co-cultivation media plates at 21° C. in dark conditions for 3 days. This may range from 1-7 days.

After the co-cultivation step, all of these embryos went through a resting step wherein they were rested on DBC3 media plus 100 mg/L carbenicillin with different concentrations of copper (culpric sulfate) in the dark at 28° C. for 3 days (this may range from 1-7 days). The original DBC3 medium (see Example 1, Medium for Plant Transformation, B Media) contains 5 µM of copper. In this example, the DBC3 media contain the same components as the original DBC3 medium except the copper. The copper (culpric sulfate) concentrations in these DBC3 media are varied from 0.1 µM, 1 µM, 2.5 µM, 4 µM to 5 µM (same as original DBC3) (Table 8). DBC3 containing 0.1 µM copper (same concentration as it in MS salt) as the negative control.

After the resting step, all of these embryos went through a selection step on the same medium as resting step (DBC3 medium plus 100 mg/L with different concentration of copper) plus 3 mg/L bialaphos in the dark at 28° C. for about 7-8 weeks. The embryos were subcultured every 2-3 weeks.

A regeneration step is followed by culturing the putative transgenic callus on PHI-RF medium plates for producing shoots and a rooting step on medium plates PHI-RR.

Transformation frequency was calculated by the number of embryos producing transgenic callus capable of regenerating plants divided by the number of embryos infected by *Agrobacterium*.

These data (Table 8) showed 1 µM copper and above increased transformation frequency 3-5 times higher than 0.1 µM copper in maize. The values provided for the concentration of copper in the various media shown below in Table 8 reflects the total concentration of copper in the medium.

TABLE 8

The transformation frequency was increased with 1 µM copper or above in maize.

| Co-cultivation media | PHI-T | | | | |
|---|---|---|---|---|---|
| | DBC3 + 100 mg/L carbenicillin+ | | | | |
| Resting media | 0.1 µM copper | 1 µM copper | 2.5 µM copper | 4 µM copper | 5 µM copper |
| | DBC3 + 100 mg/L carbenicillin + 3 mg/L bialaphos+ | | | | |
| Selection media | 0.1 µM copper | 1 µM copper | 2.5 µM copper | 4 µM copper | 5 µM copper |
| | Transformation frequency (%) | | | | |
| exp 1 | 2.5 | 15 | 12.5 | 10 | 20 |
| exp 2 | 5.0 | 17.5 | 17.5 | 17.5 | 15.0 |
| exp 3 | 2.5 | 15 | 17.5 | 12.5 | 22.5 |
| exp 4 | 7.5 | 20 | 7.5 | 7.5 | 35 |
| Average | 4.4 | 16.9 | 13.8 | 11.9 | 23.1 |

Example 15

5 µM Copper and Above Increased Transformation Frequency in Maize

Maize inbred PHR03 immature embryos (9-13 DAP when embryo size around 0.8-2.5 mm) were infected with $5 \times 10^8$ cfu/mL *Agrobacterium* LBA4404 containing superbinary vector PHPMRFP in PHI-I liquid medium. The embryos were then co-cultivated on PHI-T co-cultivation media plates at 21° C. in dark conditions for 3 days. This may range from 1-7 days.

After the co-cultivation step, all of these embryos went through a resting step wherein they were rested on DBC3 medium plus 100 mg/L carbenicillin with different concentrations of copper (culpric sulfate) in the dark at 28° C. for 3 days (this may range from 1-7 days). These DBC3 media containing different concentrations of copper are similar to those described in Example 14 except the copper concentrations are varied from 0.1 µM (as negative control), 5 µM, 10 µM, 30 µM to 50 µM.

After the resting step, all of these embryos went through a selection step on the same medium as resting step (DBC3 medium plus 100 mg/L with different concentration of copper) plus 3 mg/L bialaphos in the dark at 28° C. for about 7-8 weeks. The embryos were subcultured every 2-3 weeks.

A regeneration step is followed by culturing the putative transgenic callus on PHI-RF medium plates for producing shoots and a rooting step on medium plates PHI-RR.

Transformation frequency was calculated by the number of embryos producing transgenic plants divided by the number of embryos infected by *Agrobacterium*.

These data (Table 9) showed 5 µM copper and above increased transformation frequency 4-7 times higher than 0.1 µM copper in maize. The values provided for the concentration of copper in the various media shown below in Table 9 reflects the total concentration of copper in the medium.

TABLE 9

The transformation frequency was increased with 5 µM copper or above in maize

| Co-cultivation media | PHI-T | | | | |
|---|---|---|---|---|---|
| | DBC3 + 100 mg/L carbenicillin+ | | | | |
| Resting media | 0.1 µM copper | 5µM copper | 10 µM copper | 30 µM copper | 50 µM copper |
| | DBC3 + 100 mg/L carbenicillin + 3 mg/L bialaphos+ | | | | |
| Selection media | 0.1 µM copper | 5 µM copper | 10 µM copper | 30 µM copper | 50 µM copper |
| | Transformation frequency (%) | | | | |
| exp 1 | 5.0 | 37.5 | 35.0 | 25.0 | 27.5 |
| exp 2 | 0.0 | 30.0 | 20.0 | 7.5 | 32.5 |
| exp 3 | 0.0 | 2.5 | 0.0 | 2.5 | 7.5 |
| exp 4 | 10.0 | 15.0 | 22.5 | 12.5 | 25.0 |
| exp 5 | 0.0 | 32.5 | 17.5 | 22.5 | 12.5 |
| Average | 2.9 | 23.5 | 19.0 | 14.0 | 21.0 |

Example 16

1 µM Copper and Above Increased Transformation Frequency in Sorghum

Sorghum line TX430 immature embryos (9-15 DAP when embryo size around 0.8-2.5 mm) were infected with $1 \times 10^9$ cfu/mL *Agrobacterium* LBA4404 containing superbinary vector PHPMYFP in PHI-I liquid medium. The embryos were co-cultivated on PHI-T medium plates at 25° C. (ranged 21-25° C.) in dark for 3 days (ranged 1-7 days).

Then the embryos were transferred to DBC3+100 mg/L carbenicillin with different concentrations of copper (culpric sulfate) (same as the DBC3 media described in Example 14) at 28° C. in the dark for 7 days (ranged 1-10 days).

These embryos were transferred to the same media as previous step+3 mg/L bialaphos with various concentrations of copper. The whole selection step was in dark at 28° C. After two to three months from the initiation of the experiment, transgenic callus events were cultured for plant regeneration on the same regeneration medium (PHI-RF and PHI-Z) at the regular regeneration conditions.

Transformation frequency was calculated by the number of embryos producing transgenic callus capable of regeneration divided by the number of embryos infected by *Agrobacterium*

These data (Table 10) demonstrated that 1 μM copper and above increased the transformation frequency two times than 0.1 μM copper in sorghum. The values provided for the concentration of copper in the various media shown below in Table 10 reflects the total concentration of copper in the medium.

TABLE 10

The transformation frequency was increased with 1 μM copper or above in sorghum

| Co-cultivation media | PHI-T | | | | |
|---|---|---|---|---|---|
| | DBC3 + 100 mg/L carbenicillin+ | | | | |
| Resting media | 0.1 μM copper | 1 μM copper | 2.5 μM copper | 4 μM copper | 5 μM copper |
| | DBC3 + 100 mg/L carbenicillin + 3 mg/L bialaphos+ | | | | |
| Selection media | 0.1 μM copper | 1 μM copper | 2.5 μM copper | 4 μM copper | 5 μM copper |
| | Transformation frequency (%) | | | | |
| exp 1 | 15.0 | 30.0 | 37.5 | 36.7 | 27.5 |
| exp 2 | 5.0 | 17.5 | 17.5 | 2.5 | 25.0 |
| Average | 10.0 | 23.8 | 27.5 | 17.1 | 26.3 |

Example 17

5 μM Copper and Above Increased Transformation Frequency in Sorghum

Sorghum line TX430 immature embryos (9-15 DAP when embryo size around 0.8-2.5 mm) were infected with $1 \times 10^9$ cfu/mL *Agrobacterium* LBA4404 containing superbinary vector PHPMYFP in PHI-I liquid medium. The embryos were co-cultivated on PHI-T medium plates at 25° C. (ranged 21-25° C.) in dark for 3 days (ranged 1-7 days).

Then the embryos were transferred to DBC3+100 mg/L carbenicillin with different concentrations of copper (culpric sulfate) (same as the DBC3 media described in Example 15) at 28° C. in the dark for 7 days (ranged 1-10 days).

These embryos were transferred to the same media as previous step+3 mg/L bialaphos with various concentrations of copper. The whole selection step was in dark at 28° C. After two to three months from the initiation of the experiment, transgenic callus events were cultured for plant regeneration on the same regeneration medium (PHI-RF and PHI-Z) at the regular regeneration conditions.

Transformation frequency was calculated by the number of embryos producing transgenic plants divided by the number of embryos infected by *Agrobacterium*

These data (Table 11) demonstrated that 5 μM copper and above increased the transformation frequency 4-6 times than 0.1 μM in sorghum. The values provided for the concentration of copper in the various media shown below in Table 11 reflects the total concentration of copper in the medium

TABLE 11

The transformation frequency was increased with 5 μM copper or above in sorghum

| Co-cultivation media | PHI-T | | | | |
|---|---|---|---|---|---|
| | DBC3 + 100 mg/L carbenicillin | | | | |
| Resting media | 0.1 μM copper | 5 μM copper | 10 μM copper | 30 μM copper | 50 μM copper |
| | DBC3 + 100 mg/L carbenicillin + 3 mg/L bialaphos | | | | |
| Selection media | 0.1 μM copper | 5 μM copper | 10 μM copper | 30 μM copper | 50 μM copper |
| | Transformation frequency (%) | | | | |
| exp 1 | 3.33 | 16.67 | na | 10.00 | 5.00 |
| exp 2 | 2.50 | 15.00 | 20.00 | 10.00 | 10.00 |
| exp 3 | 0.00 | 8.33 | 10.00 | 2.50 | 10.00 |
| exp 4 | 2.50 | 15.00 | 12.50 | 12.50 | 11.11 |
| Average | 2.0 | 13.8 | 13.0 | 8.2 | 9.6 |

Example 18

Transformation in Maize Using Various Light Intensities

Maize inbred PHR03 immature embryos (9-13 DAP when embryo size around 0.8-2.5 mm) were infected with $5 \times 10^8$ cfu/mL *Agrobacterium* LBA4404 containing superbinary vector PHPMRFP in PHI-I liquid medium. The embryos were then co-cultivated on PHI-T co-cultivation media plates at 21° C. in dark conditions for 3 days. This may range from 1-7 days.

After the co-cultivation step, all of these embryos went through a resting step wherein they were rested on DBC3 media (Table 12) or DBC3 with different concentrations of copper (Table 13) plus 100 mg/L carbenicillin in the dark or dim light (10-30 μE $m^{-2}$ $sec^{-1}$) or strong light (30-50 μE $m^{-2}$ $sec^{-1}$) at 28° C. for 3 days (this may range from 1-7 days).

After the resting step, all of these embryos went through a selection step on the same medium DBC3 (Table 12) or DBC3 with different concentrations of copper (Table 13)+10 mg/L carbenicillin plus 3 mg/L bialaphos in the dark or dim light (10-30 μE $m^{-2}$ $sec^{-1}$) or strong light (30-50 μE $m^{-2}$ $sec^{-1}$) at 28° C. for about 7-8 weeks. The embryos were subcultured every 2-3 weeks.

A regeneration step was followed by culturing the putative transgenic callus on PHI-RF medium plates for producing shoots and a rooting step on medium plates PHI-RR.

Transformation frequency was calculated by the number of embryos producing transgenic plants divided by the number of embryos infected by *Agrobacterium*.

These two tables (Table 12 and 13) demonstrated that transformation frequency was not affected by light conditions during culture in maize in these experiments. The values provided for the concentration of copper in the various media shown below in Tables 12 and 13 reflects the total concentration of copper in the medium

TABLE 12

Transformation frequency of maize using various light intensities

| Co-cultivation media | PHI-T |
|---|---|

TABLE 12-continued

Transformation frequency of maize using various light intensities

DBC3 + 100 mg/L carbenicillin

| Resting media | dark | dim light | strong light |
|---|---|---|---|

DBC3 + 100 mg/L carbenicillin + 3 mg/L bialaphos

| Selection media | dark | dim light | strong light |
|---|---|---|---|

| | Transformation frequency (%) | | |
|---|---|---|---|
| exp 1 | 12.5 | 17.5 | 20 |
| exp 2 | 20.0 | 40.0 | 15.0 |
| exp 3 | 25 | 25 | 10 |
| exp 4 | 22.5 | 15.0 | 35.0 |
| exp 5 | 27.5 | 22.5 | 7.5 |
| exp 6 | 27.5 | 17.5 | 27.5 |
| Average | 22.5 | 22.9 | 19.2 |

TABLE 13

The transformation frequency of maize using various light intensities

| Co-cultivation media | PHI-T | | | |
|---|---|---|---|---|

DBC3 + 100 mg/L carbenicillin+

| | Dark | | Dim light | |
|---|---|---|---|---|
| Resting media | 2.5 μM copper | 4 μM copper | 2.5 μM copper | 4 μM copper |

DBC3 + 100 mg/L carbenicillin + 3 mg/L bialaphos+

| | Dark | | Dim light | |
|---|---|---|---|---|
| Selection media | 2.5 μM copper | 4 μM copper | 2.5 μM copper | 4 μM copper |

| | Transformation frequency (%) | | | |
|---|---|---|---|---|
| exp 1 | 12.5 | 10 | 12.5 | 10 |
| exp 2 | 17.5 | 17.5 | 17.5 | 17.5 |
| exp 3 | 17.5 | 12.5 | 15 | 15 |
| exp 4 | 7.5 | 7.5 | 10 | 27.5 |
| Average | 13.8 | 11.9 | 13.8 | 17.5 |

Example 19

Transformation in Sorghum Using Various Light Intensities

Sorghum line TX430 immature embryos (9-15 DAP when embryo size around 0.8-2.5 mm) were infected with $1 \times 10^9$ cfu/mL *Agrobacterium* LBA4404 containing superbinary vector PHPMYFP in PHI-I liquid medium. The embryos were co-cultivated on PHI-T medium plates at 25° C. (ranged 21-25° C.) in dark for 3 days (ranged 1-7 days).

Then the embryos were transferred to DBC3 with different concentrations of copper (2.5 μM, 4 μM and 5 μM)+100 mg/L carbenicillin with different concentrations of copper (culpric sulfate) at 28° C. in the dark or dim light for 7 days (ranged 1-10 days).

These embryos were transferred to the same media as previous step+3 mg/L bialaphos with various concentrations of copper. The whole selection step was in dark or dim light at 28° C. After two to three months from the initiation of the experiment, transgenic callus events were cultured for plant regeneration on the same regeneration medium (PHI-RF and PHI-Z) at the regular regeneration conditions.

Transformation frequency was calculated by the number of embryos producing transgenic plants divided by the number of embryos infected by *Agrobacterium*.

These data (Table 14) demonstrated that transformation frequency was not affected by light conditions during culture in sorghum in these experiments. The values provided for the concentration of copper in the various media shown below in Table 14 reflects the total concentration of copper in the medium

TABLE 14

The transformation frequency in sorghum using various light intensities

| Co-cultivation media | PHI-T | | | | | |
|---|---|---|---|---|---|---|

DBC3 + 100 mg/L carbenicillin+

| | Dark | | | Dim light | | |
|---|---|---|---|---|---|---|
| Resting media | 2.5 μM copper | 4 μM copper | 5 μM copper | 2.5 μM copper | 4 μM copper | 5 μM copper |

DBC3 + 100 mg/L carbenicillin + 3 mg/L bialaphos+

| | Dark | | | Dim light | | |
|---|---|---|---|---|---|---|
| Selection media | 2.5 μM copper | 4 μM copper | 5 μM copper | 2.5 μM copper | 4 μM copper | 5 μM copper |

| | Transformation frequency (%) | | | | | |
|---|---|---|---|---|---|---|
| exp 1 | 37.5 | 36.7 | 27.5 | 32.5 | 52.5 | 32.5 |
| exp 2 | 17.5 | 2.5 | 25.0 | 17.5 | 10.0 | 7.5 |
| Average | 27.5 | 17.1 | 26.3 | 25.0 | 31.3 | 20.0 |

What is claimed is:

1. A method for increasing transformation frequency in a monocot plant cell comprising:
    (a) introducing a nucleic acid into a monocot plant cell of an explant of an immature embryo by *Agrobacterium*-infection to produce an infected plant cell, wherein the plant cell is from a plant selected from the group consisting of maize, sorghum, barley, oats, rye, wheat, rice and triticale;
    (b) co-cultivating the infected plant cell for about 1 to 7 days on a co-cultivation medium comprising an auxin and about 0.1 μM copper;
    (c) culturing the infected cell for about 1 to 7 days on a resting medium to produce transformed tissue expressing the nucleic acid, wherein the resting medium comprises an auxin, a cytokinin, and about 1 μM to about 50 μM of copper, wherein transformation frequency is increased by at least 20% compared to transformation frequency of a control transformed cell that is not co-cultivated on the co-cultivation medium of (b) and not cultured on the resting medium of (c); and
    (d) regenerating the transformed tissue on a regeneration medium to produce a transformed monocot plant.

2. The method according to claim 1, wherein the copper in the co-cultivation medium or the resting medium comprises cupric sulfate, copper chloride, copper nitrate, copper gluconate, or copper acetate.

3. The method according to claim 1, comprising co-cultivating the infected cell in dark conditions of less than 10 μE m$^{-2}$ sec$^{-1}$, dim conditions of from about 10 to about 30 μE m$^{-2}$ sec$^{-1}$, or light conditions greater than 30 μE m$^{-2}$ sec$^{-1}$.

4. The method according to claim 1, comprising culturing the transformed cell in dark conditions of less than 10 μE m$^{-2}$ sec$^{-1}$, dim conditions of from about 10 to about 30 μE m$^{-2}$ sec$^{-1}$, or light conditions greater than 30 μE m$^{-2}$ sec$^{-1}$.

5. The method according to claim 1, wherein the auxin in the co-cultivation or resting medium is selected from the group consisting of 2,4-dichlorophenoxyacetic acid (2,4-D), dicamba, naphthaleneacetic acid (NAA), indoleacetic acid (IAA), picloram, 2,4,5-trichlorophenoxyacetic acid, 4-chloro-indoleacetic acid, phenylacetic acid (PAA) and indole-3-butyric acid (IBA).

6. The method according to claim 1, wherein the co-cultivation medium or resting medium comprises auxin in an amount of about 0.1 mg/L to about 10 mg/L.

7. The method according to claim 1, wherein the cytokinin in the resting medium is selected from the group consisting of 6-benzylaminopurine (BAP), zeatin, kinetin, 2iP and zeatin riboside.

8. The method according to claim 1, wherein the co-cultivation or resting medium comprises cytokinin in an amount of about 0.1 mg/L to about 10 mg/L.

9. The method according to claim 1, wherein the method further comprises selecting the transformed plant cell on selection medium, comprising copper, an auxin, a cytokinin, and a selective agent.

10. The method according to claim 9, comprising selecting the transformed cell in dark conditions of less than 10 μE m$^{-2}$ sec$^{-1}$, dim conditions of from about 10 to about 30 μE m$^{-2}$ sec$^{-1}$, or light conditions greater than 30 μE m$^{-2}$ sec$^{-1}$.

11. The method of claim 1 wherein callus initiation frequency of callus produced from the explant of an immature embryo is increased as compared to callus initiation frequency of a control callus produced from the explant of an immature embryo that is not co-cultivated on the co-cultivation medium and not cultured on the resting medium.

12. The method of claim 1 wherein the quality of calli produced from the explant of an immature embryo is improved as compared to the quality of control calli produced from an explant of an immature embryo not co-cultivated on the co-cultivation medium and not cultured on the resting medium.

13. The method according to claim 1, wherein the total time of regenerating a plant from a plant cell is shortened by about 3 months as compared to a control.

14. The method according to claim 1, wherein the plant is stably transformed.

15. A method of increasing callus initiation frequency comprising:
culturing a monocot plant cell of an explant of an immature embryo for about 1 to 7 days on a co-cultivation medium comprising an auxin and about 0.1 μM copper, wherein the monocot plant cell is from a plant selected from the group consisting of maize, sorghum, barley, oats, rye, wheat, rice, and triticale; and
culturing the monocot plant cell for about 1 to 7 days on a resting medium comprising about 1 μM to about 50 μM of copper, an auxin, and a cytokinin, to produce callus tissue, wherein callus initiation frequency is increased by at least 15% as compared to callus initiation frequency of callus produced from a control monocot plant cell of an explant that is not cultured on the co-cultivation medium and resting medium.

16. The method according to claim 15, wherein the copper in the co-cultivation medium or resting medium comprises cupric sulfate, copper chloride, copper nitrate, copper gluconate, or copper acetate.

17. The method according to claim 15, further comprising culturing the plant cell on the co-cultivation medium in dark conditions of less than 10 μE m$^{-2}$ sec$^{-1}$, dim conditions of from about 10 to about 30 μE m$^{-2}$ sec$^{-1}$, or light conditions greater than 30 μE, m$^{-2}$ sec$^{-1}$.

18. The method according to claim 15, further comprising culturing the plant cell on the resting medium in dark conditions of less than 10 μE m$^{-2}$ sec$^{-1}$, dim conditions of from about 10 to about 30 μE m$^{-2}$ sec$^{-1}$, or light conditions greater than 30 μE m$^{-2}$ sec$^{-1}$.

19. The method according to claim 15, wherein the auxin in the co-cultivation medium and resting medium is selected from the group consisting of 2,4-dichlorophenoxyacetic acid (2,4-D), dicamba, naphthaleneacetic acid (NAA), indoleacetic acid (IAA), picloram, 2,4,5-trichlorophenoxyacetic acid, 4-chloro-indoleacetic acid, phenylacetic acid (PAA) and indole-3-butyric acid (IBA).

20. The method according to claim 15, wherein the co-cultivation medium and resting medium comprises auxin in an amount of about 0.1 mg/L to about 10 mg/L.

21. The method according to claim 15, wherein the resting medium comprises the cytokinin selected from the group consisting of 6-benzylaminopurine (BAP), zeatin, kinetin, 2iP and zeatin riboside.

22. The method according to claim 15, wherein the resting medium comprises cytokinin in an amount of about 0.1 mg/L to about 10 mg/L.

23. The method according to claim 15, further comprising introducing a nucleic acid into the monocot plant cell by *Agrobacterium*-infection prior to, concomitant with, or subsequent to culturing the plant cell on the co-cultivation medium.

24. The method according to claim 23, further comprising selecting for transformed tissue expressing the introduced nucleic acid on a selection medium.

25. The method according to claim 15, further comprising regenerating the tissue into a plant.

26. The method according to claim 15, wherein the quality of calli produced from an explant of an immature embryo is improved as compared to control calli produced from an explant of an immature embryo not cultured on the co-cultivation medium and resting medium.

* * * * *